United States Patent
Botsford et al.

(10) Patent No.: US 9,610,458 B1
(45) Date of Patent: Apr. 4, 2017

(54) TREATING DISEASE WITH RESONANCE GENERATING ELECTROMAGNETIC FIELDS

(71) Applicant: Anapole Technologies Inc., Burlington, IA (US)

(72) Inventors: Stephen F. Botsford, Barrington, IL (US); Boris I. Kokorin, Moscow (RU); Joseph F. Startari, South Euclid, OH (US)

(73) Assignee: Anapole Technologies, Inc., Burlington, IA (US)

( * ) Notice: Subject to any disclaimer, the term of this patent is extended or adjusted under 35 U.S.C. 154(b) by 0 days.

(21) Appl. No.: 15/201,098

(22) Filed: Jul. 1, 2016

(51) Int. Cl.
*A61N 2/00* (2006.01)
*A61N 2/02* (2006.01)

(52) U.S. Cl.
CPC .............. *A61N 2/004* (2013.01); *A61N 2/02* (2013.01)

(58) Field of Classification Search
CPC ............... A61B 18/18; A61B 18/1815; A61B 2017/00084; A61B 2017/00039; A61N 2/00; A61N 2/004; A61N 5/00; A61N 5/02
USPC ........................................................ 600/9–15
See application file for complete search history.

(56) References Cited

U.S. PATENT DOCUMENTS

| | | | | |
|---|---|---|---|---|
| 5,658,234 | A  * | 8/1997 | Dunlavy | ................. A61N 5/02 600/9 |
| 6,503,191 | B1 * | 1/2003 | Miller | .................... A61B 18/18 600/30 |
| 2008/0021526 | A1 | 1/2008 | Kokorin | |
| 2008/0062068 | A1 | 3/2008 | Kokorin | |
| 2014/0330268 | A1 | 11/2014 | Palti et al. | |

OTHER PUBLICATIONS

Gallego, O., "Nonsurgical treatment of recurrent glioblastoma", Current Oncology, vol. 22, No. 4: e273-e281, Aug. 2015, © 2015 Multimed Inc. www.current-oncology.com.
Foletti, A., et al., "Bioelectromagnetic medicine: The role of resonance signaling", Electromagnetic Biology and Medicine, 2013; 32(4): 484-499, downloaded by University of Eastern Finland on Nov. 19, 2015, ISSN: 1536-8378 (Print) 1536-8386 (Online) Journal homepage: http://www.tandfonline.com/loi/iebm20.
Liboff, A.R., "Electric-Field Ion Cyclotron Resonance", Bioelectromagnetics, 18:85-87 (1997), © 1997 Wiley-Liss, Inc.

(Continued)

*Primary Examiner* — John Lacyk
(74) *Attorney, Agent, or Firm* — Baker & McKenzie LLP

(57) ABSTRACT

The present disclosure relates, according to some embodiments, to an electromagnetic resonance-based disease treatment system that comprises a processing unit configured to generate a resonant frequency signal and a radiating antenna configured to radiate an electromagnetic field based on the resonant frequency signal. The resonant frequency signal may carry at least one frequency at which reference materials related to a disease condition resonate. An antenna configuration may be used to determine one or more resonant frequencies of the reference materials. A subject having or at risk of having the disease condition may be exposed to the electromagnetic field in order to treat the disease condition.

14 Claims, 25 Drawing Sheets

(56) References Cited

OTHER PUBLICATIONS

Deorah, S., MA, et al., Trends in brain cancer incidence and survival in the United States: Surveillance, Epidemiology, and End Results Program, 1973 to 2001, Neurosurg. Focus, vol. 20, Apr. 2006, 7 pages.
Stavroulakis, P., "Biological Effects of Electromagnetic Fields", © Springer-Verlag Berlin Heidelberg 2003, pp. 76-113.
Hegi, M.E., Ph.D., et al., "MGMT Gene Silencing and Benefit from Temozolomide in Glioblastoma", The New England Journal of Medicine, 352; 10, 7 pages, www.NEJM.org, Mar. 10, 2005, Downloaded from nejm.org at SUNY Albany on Oct. 12, 2016, Copyright © 2005 Massachusetts Medical Society.
Duntze, J., MD, et al., "Implanted Carmustine Wafers Followed by Concomitant Radiochemotherapy to Treat Newly Diagnosed Malignant Gliomas: Prospective, Observational, Multicenter Study on 92 Cases", Annals of Surgical Oncology, Official Journal of the Society of Surgical Oncology, (2013) 20:2065-2072, © Society of Surgical Oncology 2012.
Jackson, J.D., "Simple Radiating Systems, Scattering, and Diffraction", Classical Electrodynamics, Second Edition, Section 9, 10 pages, Copyright © 1962, 1975, by John Wiley & Sons, Inc.
Miller, M.A., "Charge and current electrostatics. Nonstationary sources of static fields", Methodological Notes, Institute of Applied Physics, Academy of Sciences of the USSR, Gor'kii, Usp., Fiz. Nauk 142, 147-158 (Jan. 1984), 8 pages.
Wait, S.D., et al., "Polymeric drug delivery for the treatment of glioblastoma", Neuro-Oncology, 17(S2), ii9-ii23, 2015, Published by Oxford University Press on behalf of the Society for Neuro-Oncology.
Smith, S.D., et al., "Effects of resonance magnetic fields on chick femoral development in vitro", Journal of Bioelectricity, 10(1&2), 81-99 (1991), Copyright © 1991 by Marcel Dekker, Inc.
Jun, H. Toni, et al., "ANG 102, A Fully Human Anti-Hepatocyte Growth Factor/Scatter Factor Neutralizing Antibody, Enhances the Efficacy of Temozolomide or Docetaxel in U-87 MG Cells and Xenografts", Cancer Therapy: Preclinical, Clin Cancer Res 2007;13(22) Nov. 15, 2007, Downloaded from clincancerres.aacrjournals.org on Jan. 22, 2016, © 2007 American Association for Cancer Research, www.aacrjournals.org.
Kirson, E.D., et al., "Disruption of Cancer Cell Replication by Alternating Electric Fields", Cancer Research, The Journal of Cancer Research (1916-1930) | The American Journal of Cancer (1931-1940), © 2004 American Association for Cancer Research, [Cancer Research 64, 3288-3295, May 1, 2004].
Regling, C., et al., "Evidence for ICR Magnetic Field Effects on Cartilage and Bone Development in Embryonic Chick Bone Explants", 48th Annual Meeting of the Orthopaedic Research Society, Poster No. 0379, 2002, 1 page.
Gathiram, Prem, PhD, et al., "Effects of a Unique Electromagnetic Field System on the Fertility of Rats", Archives of Environmental & Occupational Health, vol. 64, No. 1, 2009, 8 pages, Copyright © 2009 Heldref Publications.
McLeod, B.R., et al., "Calcium and Potassium Cyclotron Resonance Curves and Harmonics in Diatoms (A. Coffeaeformis)", Journal of Bioelectricity, 6(2), 153-168 (1987), Copyright © 1987 by Marcel Dekker, Inc.
Tang, H., et aL, "Interaction of hsa-miR-381 and glioma suppressor LRRC4 is involved in glioma growth", Brain Research 1390 (2011) 21-32, available at www.sciencedirect.com and www.elsevier.com/locate/brainres.
Ryaby, J.R., et al., "Prevention of experimental osteopenia by use of combined AC/DC magnetic fields", Electricity and Magnetism in Biology and Medicine, San Francisco Press, San Francisco, Issue: 1993b, pp. 371-374 [807-810], 1993.
Clark, M.J., et al., U87MG Decoded: The Genomic Sequence of a Cytogenetically Aberrant Human Cancer Cell Line, PLoS Genetics | www.plosgenetics.org, Jan. 2010 | vol. 6 | Issue 1 | e1000832, 17 pages.
Francescone, R.A., et al., "Role of YKL-40 in the Angiogenesis, Radioresistance, and Progression of Glioblastoma", The Journal of Biological Chemistry vol. 286, No. 17, pp. 15332-15343, Apr. 29, 2011 © 2011 by The American Society for Biochemistry and Molecular Biology, Inc.
Goloudina, A.R., et al., "Inhibition of HSP70: A challenging anti-cancer strategy", Cancer Letters 325 (2012), 117-124, Journal homepage: www.elsevier.com/locate/canlet.
Li, G., et al., "HSP70 Protein Promotes Survival of C6 and U87 Glioma Cells by Inhibition of ATF5 Degradation", The Journal of Biological Chemistry vol. 286, No. 23, pp. 20251-20259, Jun. 10, 2011 © 2011 by The American Society for Biochemistry and Molecular Biology, Inc.
Formolo, C.A., et al., "Secretome Signature of Invasive Glioblastoma Multiforme", Journal of Proteome Research, 2011, 10, 3149-3159, ACS Publications © 2011 American Chemical Society.
ICNIRP Guidelines, "Guidelines for Limiting Exposure to Time-Varying Electric, Magnetic, and Electromagnetic Fields (Up to 300 GHz)", Health Physics, Apr. 1998, vol. 74, No. 4, 34 pages.
Lacouture, M.E., et al., "Characterization and Management of Dermatologic Adverse Events With the NovoTTF-100A System, a Novel Anti-mitotic Electric Field Device for the Treatment of Recurrent Glioblastoma", Seminars in Oncology, vol. 41, No. 3, Suppl 4, Jun. 2014, pp. S1-S14.
Zeng, A., et al., "IDH1/2 mutation status combined with Ki-67 labeling index defines distinct prognostic groups in glioma", Oncotarget, vol. 6, No. 30, 2015, www.impactjournals.com/oncotarget/, 7 pages.
Suva, M.L., et al., "Reconstructing and Reprogramming the Tumor-Propagating Potential of Glioblastoma Stem-like Cells", Cell 157, 580-594, Apr. 24, 2014 © 2014 Elsevier Inc.
Koh, Y., et al., "Detection of a Distinctive Genomic Signature in Rhabdoid Glioblastoma, A Rare Disease Entity Identified by Whole Exome Sequencing and Whole Transcriptome Sequencing1,2,3", Translational Oncology, vol. 8, No. 4, Aug. 2015, pp. 279-287.
Hashizume, R., et al., "Morphologic and molecular characterization of ATRT xenografts adapted for orthotopic therapeutic testing", Neuro-Oncology 12(4):366-376, 2010.

\* cited by examiner

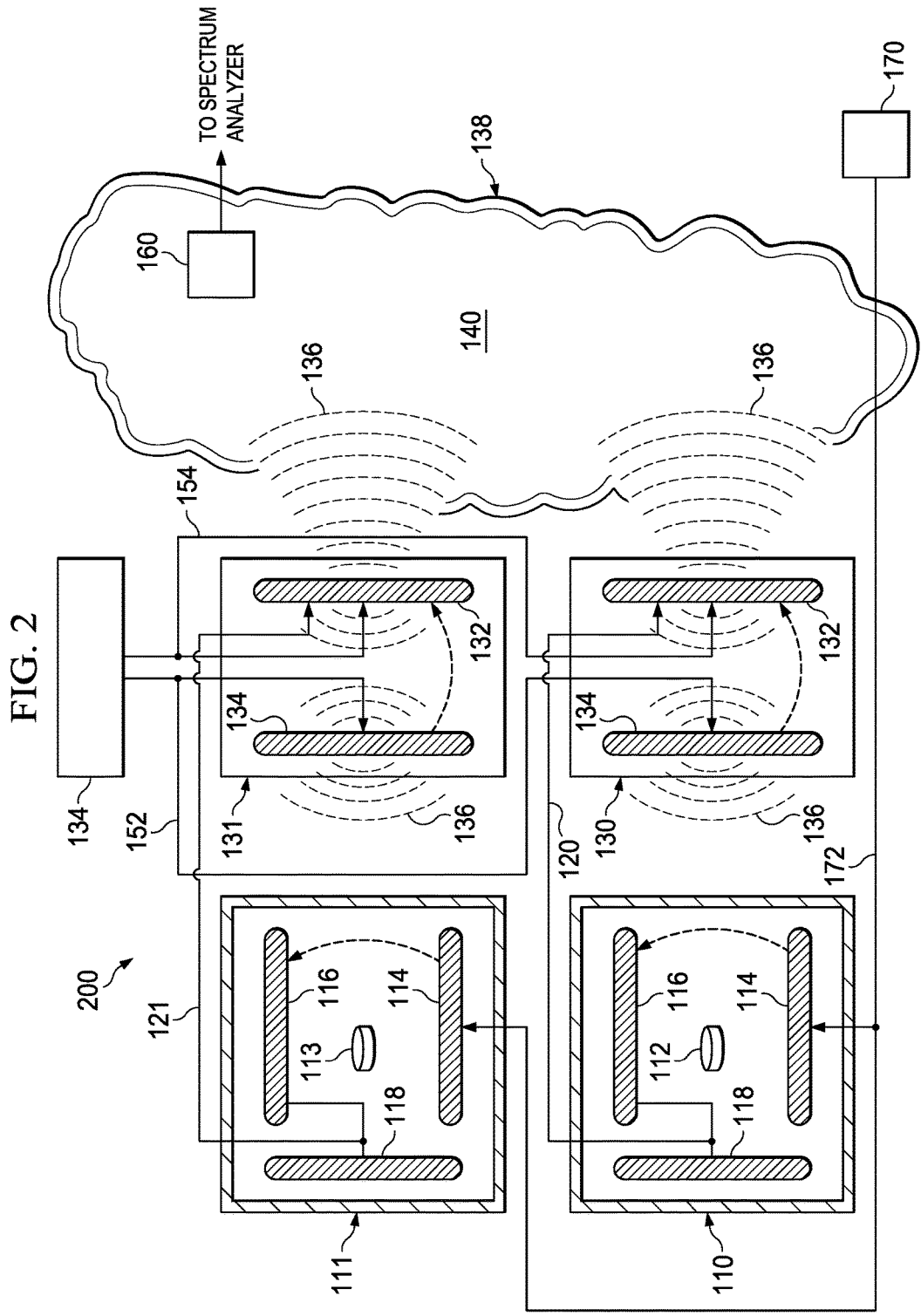

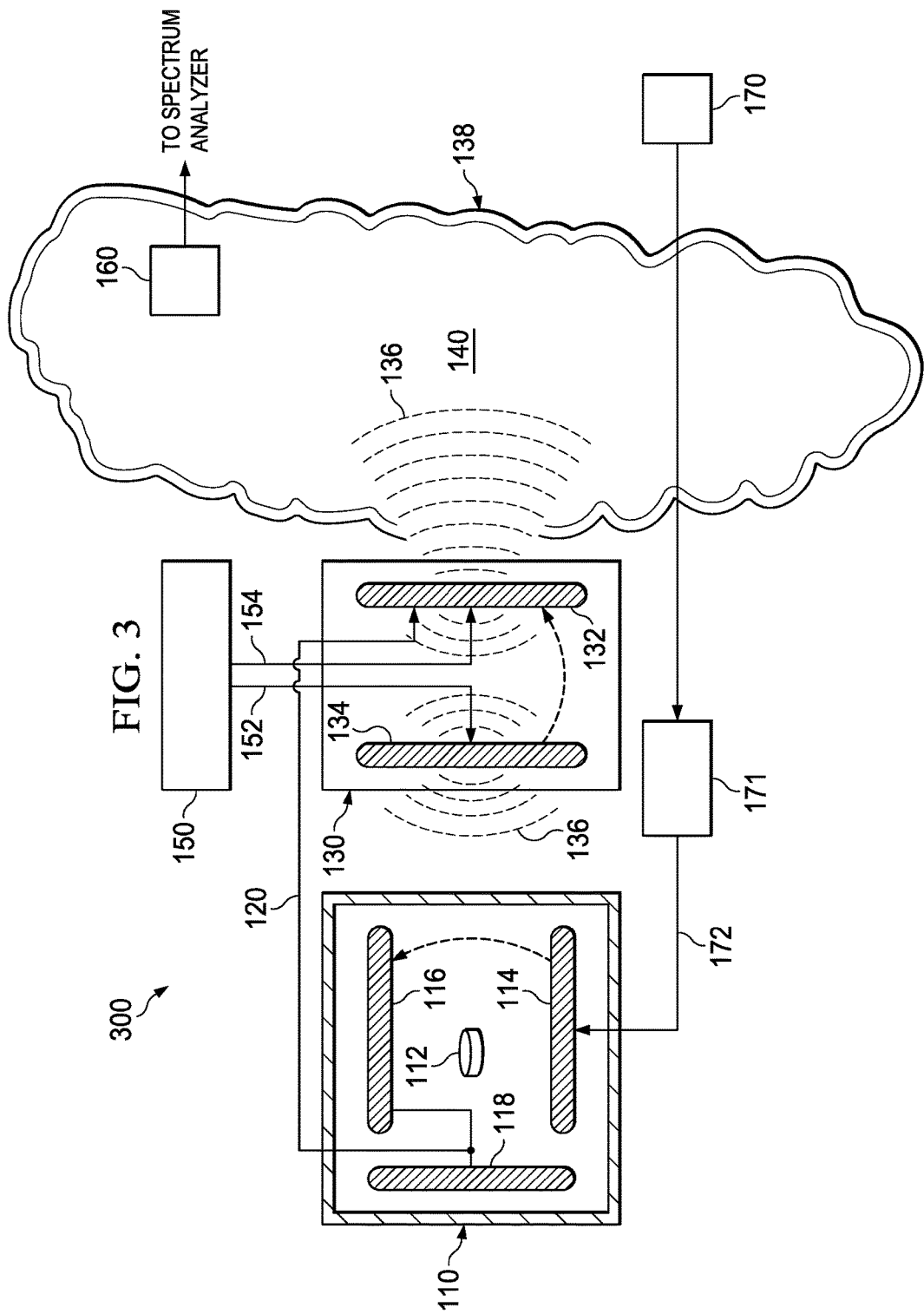

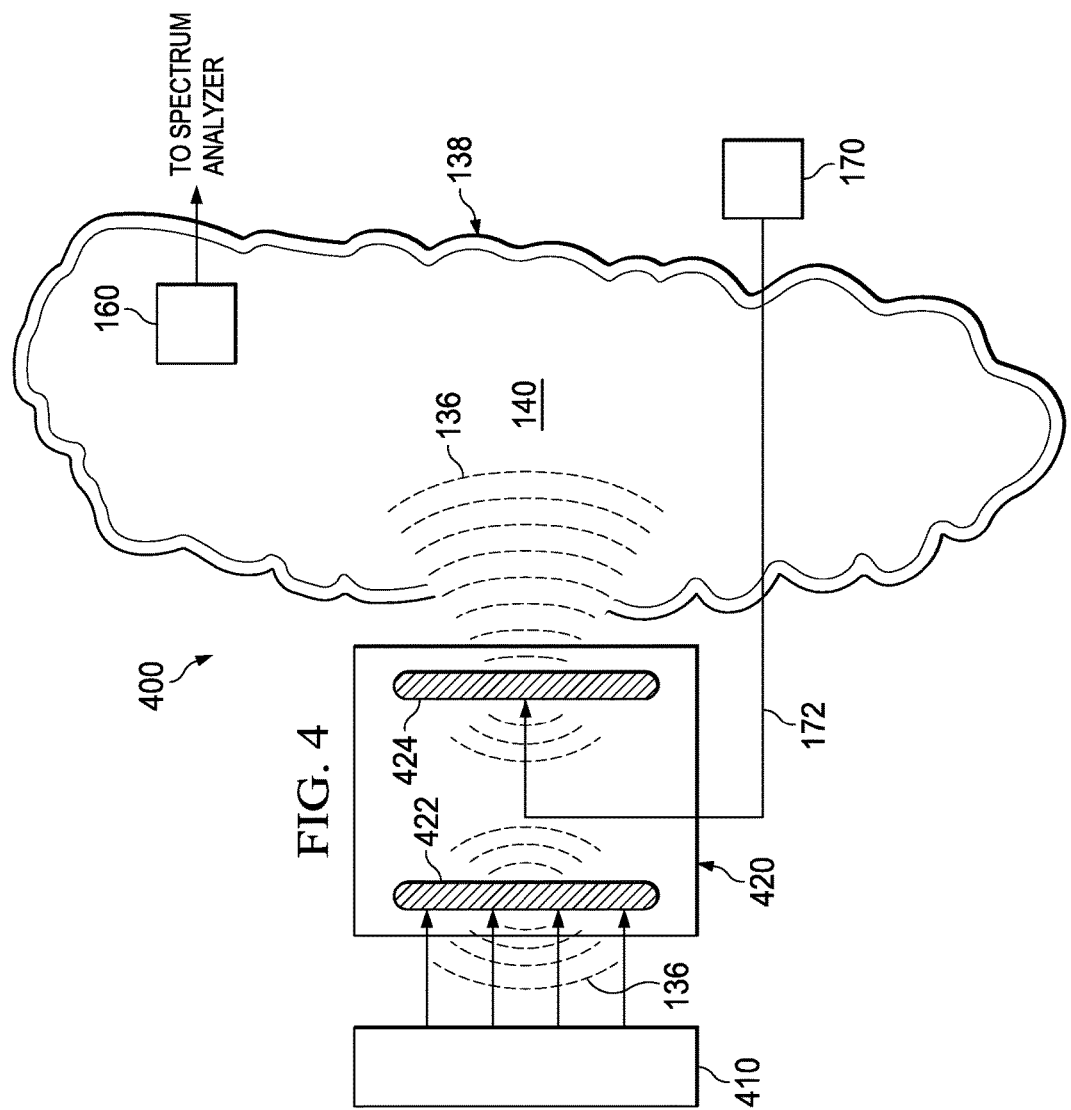

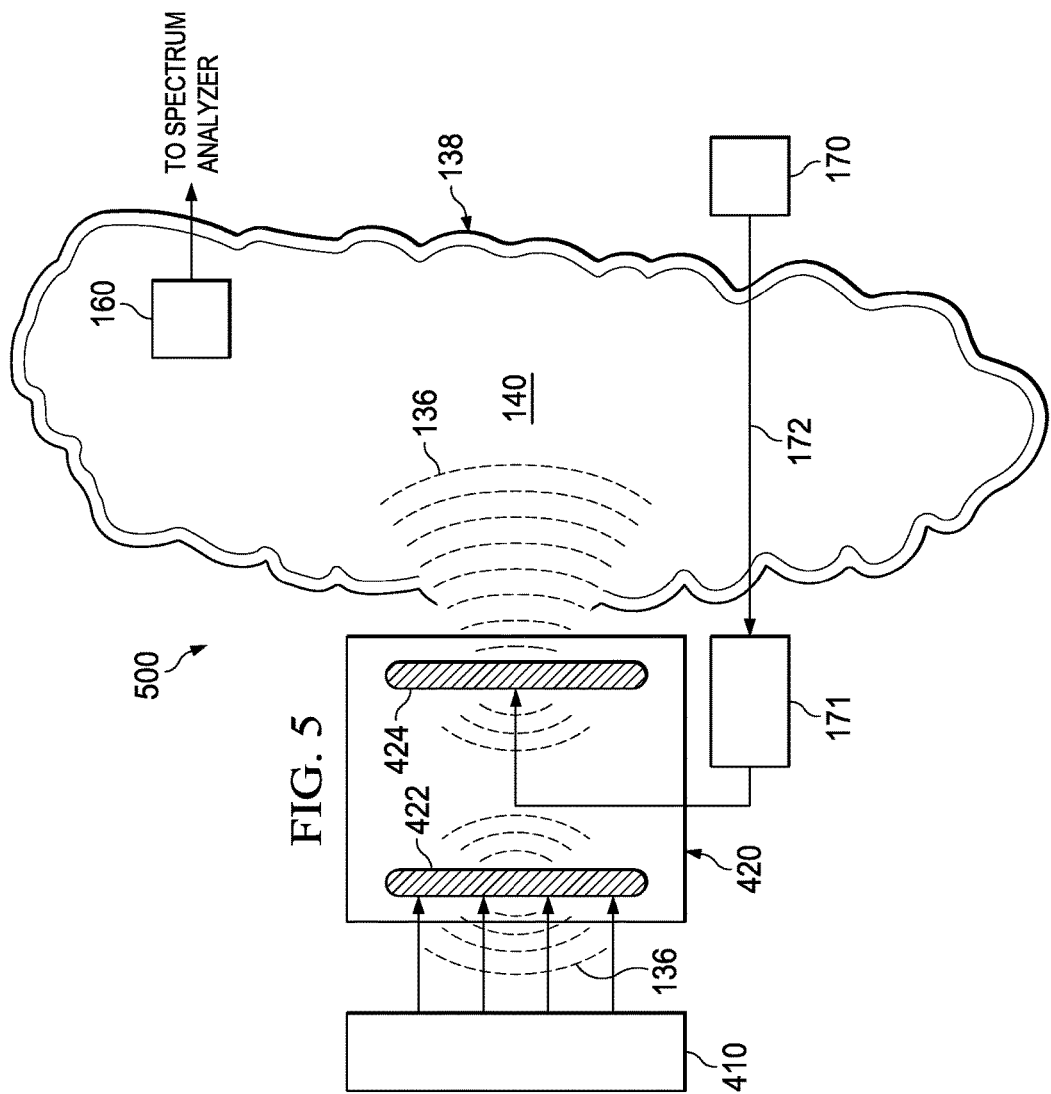

TREATING DISEASE WITH RESONANCE GENERATING ELECTROMAGNETIC FIELDS

TECHNICAL FIELD

The present disclosure relates, in some embodiments, to treat human and/or non-human animal disease conditions involving resonance-based electromagnetic radiation.

BACKGROUND

Glioblastoma multiforme (GBM) is an aggressive primary tumour that arises in the glial cells of the brain, and accounts for approximately half of all brain tumours. GBM is relatively rare with an incidence of approximately three cases per 100,000 person-years. However, the aggressive nature of the disease and the limited treatment options combine to negatively impact overall survival. Current standardized first-line treatment for GBM may comprise surgical resection (debulking), followed by six weeks of radiotherapy and concurrent chemotherapy with an alkylating agent, temozolomide. Even with this aggressive regimen, which is associated with considerable morbidity, median survival time after a standard primary intervention is less than a year, with less than 5% of patients surviving for five years. Since many GBM tumours are resistant to temozolomide due to methylation by the O6-methylguanine DNA methyl transferase (MGMT) gene, there has been a continuing search for new chemotherapeutic agents that can induce apoptosis in GBM tumours, particularly for second-line treatments. Example efforts include intralesional implantation of carmustine wafers, antiangiogenic therapies with a humanized monoclonal antibody targeting the HGF/SF:cMet axis, and methods using low intensity, intermediate frequency alternating electric fields (TTFields) to induce cell cycle arrest and cell death in tumours.

SUMMARY

A need has arisen for improved approaches to treating conditions such as GBM by using non-invasive modulated electromagnetic radiations that avoids cumbersome calculations and trial-and-error tests.

The present disclosure relates, according to some embodiments, to methods of administering to a subject having or at risk of having a disease condition with resonance-based electromagnetic radiation. For example, a method may comprise selecting one or more reference materials related to the disease condition; capturing one or more resonant frequencies of the reference materials; generating a resonant frequency signal comprising at least one of the captured resonant frequencies; radiating an electromagnetic field based on the resonant frequency signal; and exposing the subject to the electromagnetic field to affect biological activities of cells related to the disease condition.

In some embodiments, a method may comprise generating a modulated broadband signal that is simultaneously modulated in a signal generator by a first waveform at a first frequency and at least a second waveform at a second frequency. An electromagnetic field may be effectuated based on both a resonant frequency signal and a modulated broadband signal.

In some embodiments, a method may comprise generating, by a signal generator, a booster signal. The booster signal may comprise a single, low frequency waveform having a frequency lower than 100 KHz. An electromagnetic field may be effectuated further based on the booster signal. In some embodiments, the first frequency of the first waveform may be substantially identical with the low frequency of the booster signal but different from the second frequency of the second waveform. In some embodiments, the modulated broadband signal has a bandwidth of 1 MHz or greater, and the first frequency of the first waveform is about 1 Hz or about 4 Hz, whereas the second frequency of the second waveform is less than 1 MHz.

In some embodiments, a method may further comprise selecting one or more second reference materials related to the disease condition; capturing one or more second resonant frequencies of the second reference materials; generating a second resonant frequency signal comprising at least one of the captured second resonant frequencies; radiating a second electromagnetic field based on the second resonant frequency signal; and exposing the subject to the second electromagnetic field simultaneously with exposure to the electromagnetic field.

In some embodiments, a method may comprise tuning frequencies of the electromagnetic field via a feedback loop to maximize resonance of the reference materials.

In some embodiments, reference materials may be critical to the function, progression, viability, and/or continuation of a cell or organism causing or associated with a disease condition. Sometimes, after selecting reference materials but before capturing one or more resonant frequencies, reference materials may be placed and isolated inside a shielded container. In some embodiments, a resonant frequency signal comprises at least two captured resonant frequencies, including any harmonics that are used simultaneously to expose the subject.

In some embodiments, a modulated broadband signal may be received by a first broadband antenna via cable, and a booster signal and a resonant frequency signal may be received by a second broadband antenna via cables. An electromagnetic field used to expose the subject may be effectuated based on radiations from both the first and second broadband antennae, which are coupled in an antenna box. In some embodiments, the exposure of the subject to the electromagnetic field may last for a sufficient cumulative period of time to cause death of cells related to the disease condition or slow the progression of the disease condition.

In some embodiments, a disease condition may relate to Glioblastoma Multiforme (GBM). Here reference materials may be selected from a group, for example, of hsa-miRNA-38, mutated alpha-kinase 2 gene, Hsp70 (70 kDa heat shock protein), CHI3L1 (chitinase-3-like protein 1), and GBM cells.

In some embodiments, a disease condition may relate to *Mycobacterium Tuberculosis* (Mtb). Here reference materials may be selected from a group, for example, of Phosphatidylmyo-inositol Mannosides (PIM), Arabinogalactan, Lipoarabinomannan (LAM), and Alpha-crystallin.

In some embodiments, a disease condition may relate to Human Immunodeficiency Virus (HIV). Here reference materials may be selected from a group, for example, of gp120, gp41, gp160, Gag polyprotein, Env protein, sequences of viral RNA, p24 protein, and pro-viral DNA.

The present disclosure relates, in some embodiments, to an electromagnetic resonance-based disease treatment system. A system may comprise a processing unit configured to generate a resonant frequency signal that carries at least one frequency at which reference materials related to a disease condition resonate; and a radiating antenna configured to radiate an electromagnetic field based on the resonant frequency signal. An electromagnetic field may be operable on a subject having or at risk of having the disease condition by exposing the subject to the electromagnetic field in order to treat the disease condition.

In some embodiments, a processing unit may comprise a signal generator configured to generate a modulated broadband signal at least via simultaneously modulation by a first waveform at a first frequency and at least a second waveform at a second frequency. An electromagnetic field may be effectuated based on both the resonant frequency signal and the modulated broadband signal.

In some embodiments, a signal generator is further configured to generate a booster signal comprising a single, low frequency waveform below about 100 KHz. An electromagnetic field may be further based on the booster signal. In some embodiments, the first frequency of the first waveform is substantially identical with the low frequency of the booster signal but different from the second frequency of the second waveform. In some embodiments, a resonant frequency signal may carry a plurality of resonant frequencies that are used simultaneously to expose the subject.

In some embodiments, a processing unit may comprise a multi-frequency signal generator or multiple single frequency signal generators configured to generate a plurality of resonant frequencies based on calculated, digitized, or measured resonant frequencies of the reference materials.

In some embodiments, a system may comprise a feedback antenna located in a near field zone of the subject and an amplifier coupled to the feedback antenna and a radiating antenna. A feedback antenna, an amplifier, and a radiating antenna may form a feedback loop operable to tune frequencies of the electromagnetic field.

The present disclosure relates, in some embodiments, to an apparatus for administering to a subject a resonance-based electromagnetic radiation. The apparatus may comprise a container configured to hold a one or more target substances related to a disease condition and an antenna configuration configured to determine at least one resonant frequency at which the target substances resonate.

In some embodiments, an apparatus may comprise a processing unit coupled to an antenna configuration and configured to generate a modulated broadband signal that is simultaneously modulated at two frequencies of two different waveforms and a resonant frequency signal encompassing the at least one resonant frequency. An apparatus may further comprise a radiating antenna configured to radiate a modulated electromagnetic field based on the modulated broadband signal and the resonant frequency signal, wherein the modulated electromagnetic field is operable to expose the subject.

The present disclosure relates, in some embodiments, to a system for administering to a subject a resonance-based electromagnetic radiation. The system may comprise means for selecting one or more target substances relevant to a disease condition and means for determining at least one resonant frequency at which the target substances resonate.

In some embodiments, a system may comprise means for generating a broadband signal that is simultaneously modulated at two frequencies of two different waveforms and a resonant frequency signal comprising the at least one resonant frequency; means for radiating an electromagnetic field based on the broadband signal and the resonant frequency signal; and means for exposing a subject carrying the disease condition to the electromagnetic field to affect biological activities of cells relevant to the disease condition.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

Some embodiments of the disclosure may be understood by referring, in part, to the present disclosure and the accompanying drawings, wherein:

FIG. 7A illustrates an example frequency spectrum captured using *Bacillus* Calmette-Guerin (BCG), an attenuated strain of *Mycobacterium bovis*, as a reference material;

FIG. 7B illustrates another example frequency spectrum captured using reference materials related to Glioblastoma Multiforme (GBM).

FIG. 7B-1 illustrates, individually, the first of five traces shown in FIG. 7B which represents the spectral difference between cycle 7 and the average of five cycles taken at the 2 hour point.

FIG. 7B-2 illustrates, individually, the second of five traces shown in FIG. 7B which represents the spectral difference between cycle 6 and the average of five cycles taken at the 2 hour point.

FIG. 7B-3 illustrates, individually, the third of five traces shown in FIG. 7B which represents the spectral difference between the average of five cycles taken at the 2 hour point and itself.

FIG. 7B-4 illustrates, individually, the fourth of five traces shown in FIG. 7B which represents the spectral difference between cycle 5 and the average of five cycles taken at the 2 hour point.

FIG. 7B-5 illustrates, individually, the fifth of five traces shown in FIG. 7B which represents the spectral difference between cycle 4 and the average of five cycles taken at the 2 hour point.

FIG. 10A shows changes in U-87 MG cell number;

FIG. 10B shows changes in U-87 MG cell cycle;

FIG. 10C shows changes in DNA fragmentation in U-87 MG in all four quadrants of a histogram;

FIG. 10D shows changes in caspase-3/7 activation;

FIG. 10E shows changes in phosphotidylserine (PS) as measured by Annexin V staining;

FIG. 11A shows changes in U-87 MG cell number;

FIG. 11B shows changes in U-87 MG cell cycle;

FIG. 11C shows changes in DNA fragmentation in U-87 MG in all four quadrants of a histogram;

FIG. 11D shows changes in caspase-3/7 activation;

FIG. 11E shows changes in PS as measured by Annexin V staining;

FIG. 12A shows changes in U-87 MG cell number;

FIG. 12B shows changes in U-87 MG cell cycle, including the sub G0 population;

FIG. 12C shows changes in DNA fragmentation in U-87 MG in all four quadrants of a histogram;

FIG. 12D shows changes in caspase-3/7 activation;

FIG. 12E shows changes in PS as measured by Annexin V staining; and

DETAILED DESCRIPTION

The present disclosure relates, in some embodiments, to systems, apparatuses, and methods for treating a condition (e.g., a disease condition) by exposing a target (e.g., a DNA sequence, a protein, an enzyme, a mineral etc. within a cell, a tissue, an organ or the body, etc. which is associated with the disease condition) to a modulated electromagnetic field including resonant frequencies at which at least a portion of the target resonates. The present disclosure also relates to discovery of resonant frequencies for any given disease condition.

Substances may exhibit resonance at a fundamental frequency and at specific harmonic frequencies when exposed to static or time-varying magnetic fields. Resonant frequencies for a particular substance may vary depending on field strength and modulation.

According to some embodiments, determining resonant frequencies does not involve cumbersome calculation and trial-and-error to induce resonance in a selected substance. In an example process, first, one or more biological substances critical to the progression of a particular disease condition may be selected and isolated. Then, one or more resonant frequencies of the selected target substance(s) may be measured and captured by using the substance(s) as a source material or reference material (sometimes referred to herein simply as a reference or source). After determination, one or more resonant frequencies may be transmitted by means of broadband transmission. A positive feedback loop may be optionally employed to amplify and tune a developed external electromagnetic field. Further, once an electromagnetic field is tuned, it may be used to expose a subject (e.g., cells, animals, and/or patients having or at risk of having a target disease such as cancer, virus, bacteria, degenerative condition or other malady). The tuned external field may be located within a near field zone of an antenna array. Therefore, a disease condition may be treated with resonance generating electromagnetic fields by targeting substances relevant to the condition (e.g., key to the function, progression, viability, proliferation, continuation, and/or survival of the disease) to which this therapy is applied.

According to some embodiments, multiple reference materials may be used concurrently with an appropriate antenna configuration or arrangement. When treating a disease, prolonged exposure of a subject to a tuned electromagnetic field may induce amplified resonance within target substances, which in turn helps stop a disease. Amplified resonance may also be induced in a target substance by simultaneous transmissions of multiple single-frequency signals identified and captured by methods disclosed herein. A modulated electromagnetic field disclosed herein is non-invasive and does not require electrodes or other attachments to be connected to a subject in order to deliver therapy.

Figure 1:
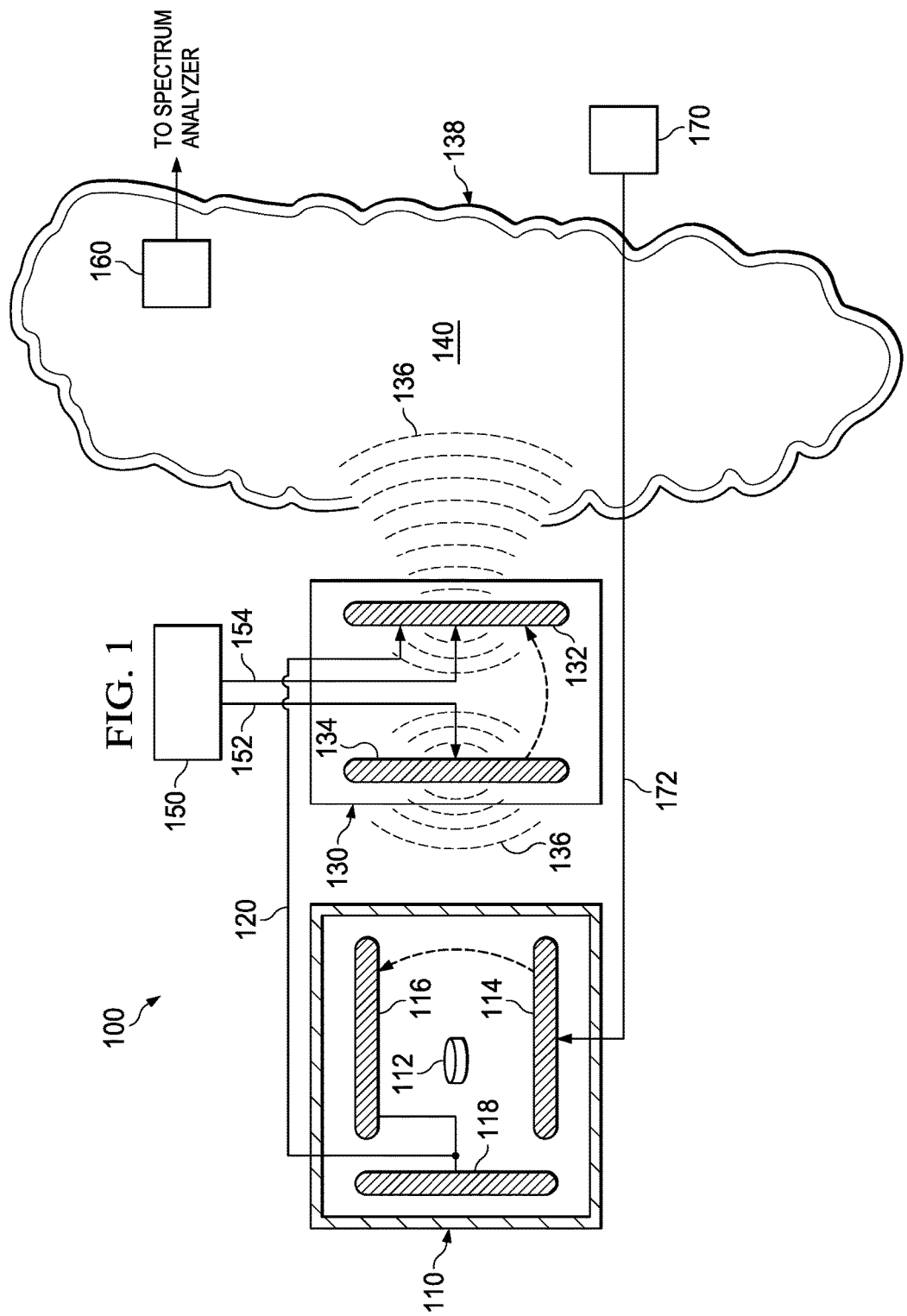
FIG. 1 illustrates a disease treatment system that may transmit a resonant frequency according to a specific example embodiment of the disclosure.

FIG. 1 illustrates disease treatment system 100 according to a specific example embodiment of the disclosure, where a disease may be treated with targeted electromagnetic radiation. Disease treatment system 100 comprises shielded container 110, broadcast antenna box 130, signal generator 150, monitoring antenna 160, and feedback antenna 170, arranged as shown in FIG. 1. Disease treatment system 100 may represent a single line broadband setup since one signal line 1 resonant frequency signal.

As shown in FIG. 1, shielded container 110 may be configured to hold one or more reference materials (e.g., reference material 112) that are relevant to a disease condition. A suitable quantity of reference material 112 may be extracted from biological cells of a subject that carries a disease condition to be treated. This subject may be subject 140 to be treated or may be a different subject. In some embodiments, biological and/or other substances critical to the function or progression of the disease condition are selected to be targeted. Compared to man-made organic materials, reference material 112 may be advantageous, for example, where resonant frequencies (e.g., exact resonant frequencies) may be determined accurately by testing actual biological substances of a disease or other substances (e.g., calcium, iron, etc.) key to the function, progression, viability, proliferation, continuation, and/or survival of a disease condition. Further, reference material 112 may capture and/or fine-tune resonant frequencies of biological and/or other substances with little or no activity as a bandpass filter. For example, reference material 112 may act as a tuning fork that absorbs radiated frequencies and resonates at one or more certain frequencies. Selected substances, such as those in reference material 112, may be isolated and placed in a non-conductive vial (e.g., glass vial). A vial may be seated within a capsule to ensure proper positioning within shielded container 110. Although container 110 is shown as electromagnetically "shielded," any suitable type of container (e.g., open or closed) may be used as long as the purpose of resonant frequency determination can be fulfilled.

Shielded container 110 may further comprise (or be coupled to) one or more of antennae 114, 116, and 118, which are configured to determine or capture one or more resonant frequencies of reference material 112. Antenna 114 serves as a broadband-compatible driven antenna, while antenna 116 and 118 serve as broadband-compatible receiving antennae. For instance, reference material 112 may be properly positioned between driven antenna 114 and receiving antennae 116 and 118. One or more resonant frequency signals are captured within a feedback loop as system 100 tunes. Signal spectra can be recorded through the use of a spectrum analyzer, an oscilloscope, and/or proprietary software (e.g., SPAN 32), thus one or more resonant frequencies may be captured within system 100 and within the software (e.g., for further use). These various signals, including resonant frequency bands, may be digitized and stored electronically. Resonant frequency signal 120 may be implemented as any signal comprising carrying one or more captured resonant frequencies and may be delivered to broadcast antenna box 130.

As shown in FIG. 1, signal generator 150 may be a multi-channel (broadband and single frequency) signal generator that supplies modulated signals to radiating antennae 132 and 134. In an example embodiment, signal generator 150 generates two signals, including modulated broadband signal 152 and single-frequency modulated signal 154, that feed into broadcast antenna box 130. Modulated broadband signal 152 may have a bandwidth of one Mega-Hertz (MHz) or greater. A lower-end frequency of modulated broadband signal 152 may be flexibly determined to have any suitable value (e.g., with the lowest frequency no less than 1 Hz, no less than 3 Hz, no less than 10 Hz, or no less than 100 Hz). In an example, modulated broadband signal 152 has various frequency components between 100-3500 MHz. Modulated broadband signal 152 may be simultaneously modulated by at least two different waveforms, each at its own frequency. In an example, modulated broadband signal 152 may be simultaneously modulated by a first sinusoidal waveform (e.g., with a frequency of 1 Hz, 4 Hz, or 16 Hz, etc.) along with modulation by a second waveform at a different frequency than the first modulating signal, making signal 152 a double-modulated broadband signal. Simultaneous modulation of a broadband signal 152 by at least two waveforms occurs inside signal generator 150, and such a design may help enhance amplified resonance. For example simultaneous modulations via a triangle waveform along with a square waveform may produce increased amplified resonance. Further, an additional single-frequency modulated signal 154 is an optional booster signal, which may be flexibly determined to have any suitable value and may be implemented as a single, lower frequency (e.g., 1 Hz, or 4 Hz, or 16 Hz, or below 1 KHz, or below 100 KHz (such as 2.2 KHz), etc.) waveform without any higher frequency components. The single, low frequency waveform via separate transmission may also enhance amplified resonance.

Signals supplied by signal generator 150 may be at very low, low, high, or very high frequencies and may be simultaneously modulated by at least two frequencies (very low, low, high, very high, low and high, or any other combination thereof) with different and/or similar waveforms. For instance, signal generator 150 may supply broadband signal 152—e.g., with a bandwidth of 1 MHz or greater which is modulated by at least two different waveforms plus an optional booster signal 154 at a single low frequency. A first waveform of broadband signal 152 may be substantially identical to booster signal 154 and a second waveform of broadband signal 152 may have a different frequency than booster signal 154. Such waveform combinations may optimize resonance within the targeted areas of a disease condition.

System 100 may operate with any non-ionizing frequency range and at low field or high field emission levels. Low field transmission strength and modulation typically within radio frequency (RF) to low microwave frequency range of any suitable frequency end points (e.g., 0 Hz to 6 GHz, 100 MHz to 3.5 GHz, or 3 Hz to 10 GHz, etc.) may be used to minimize any potential negative side effects of the therapy. The larger the bandwidth of transmission, the higher the number of resonant frequencies (including harmonics) that can be captured and applied for disease treatment.

As shown in FIG. 1, broadcast antenna box 130 may comprise broadband antennae 132 and 134. Broadband antenna 132 is configured to receive resonant frequency signal 120 by cable from broadband antenna 116 and/or broadband antenna 118. Resonant frequency signal 120 is mixed by cable with modulated broadband signal 152 (modulated by at least two different waveforms at different frequencies simultaneously) and with single-frequency modulated booster signal 154, if present, which is transmitted in space both inside and outside broadcast antenna box 130 to generate modulated broadband electromagnetic signal 136. Broadband antennae 132 and 134 radiate signals to form the mixed modulated broadband electromagnetic signal 136, which effectuates an electromagnetic field onto subject 140. Subject 140 may be a patient, an animal, a cell culture, or any applicable disease carrier. Exposing subject 140 carrying a disease to the resonance generating electromagnetic field would affect biological activities of cells or organisms (e.g., inhibit progression or growth, or cause death) that are relevant to the disease. Note that broadcast antenna box 130 may not require the use of mixer, amplifier, internal feedback antenna, or a stabilizing inner core. Instead, broadcast antenna box 130 may employ one or more external feedback antennae, which may not only boost a signal at a distance but also enhance electromagnetic field uniformity.

In some embodiments, disease treatment system 100 may further comprise feedback antenna 170, which is connected to shielded container 110 to form a feedback loop. Feedback antenna 170 may be a broadband-capable antenna that receives radiated signal 136 and accordingly generates feedback signal 172. Therefore, Feedback antenna 170 supplies signal 136 back to shielded container 110 to induce feedback resonance within shielded container 110 and subsequently in radiated antenna(s) 132 and/or 134. For example, radiated signal 136 may be supplied to shielded container 110 by means of a positive feedback loop to induce resonance within selected reference material 112. A broadband signal (e.g., signal 120) that carries captured resonances from reference material 112 may be then supplied to radiating antenna 132 as part of the feedback loop.

Both generated electromagnetic signals and signals carrying the specific resonances may be radiated, and such radiation may repeat. The repetitive feedback action may amplify resonances specific to reference material 112 and may quickly cause an external electromagnetic field to reach steady state. For example, as shown in FIG. 1, in an embodiment with a single reference material and antenna set up, signals from antennae 132 and 134 may be first radiated as separate signals. Then, as a result of a feedback loop, signals from antennae 132 and 134 may be radiated as mixed signal 136, which is reinforced by received mixed transmission from the feedback antenna(e) and reinforced by mixing with the reference/source material signal. An external electromagnetic field formed between feedback antenna 170 and radiating antenna 132 may also be referred to as near-field zone or area 138 of an antenna array. After reaching a steady state, an external electromagnetic field is considered "tuned," which may be confirmed by use of monitoring antenna 160 and a spectrum analyzer in conjunction with proprietary software (SPAN 32), which records correlation factors between scans. The electromagnetic field may also be monitored by using an oscilloscope. For example, monitoring antenna 160 (e.g., a broadband antenna) may monitor a spectral profile of signal 136 and then send the profile to a spectrum analyzer for analysis, e.g., in terms of component frequencies and magnitudes.

Figure 7A:
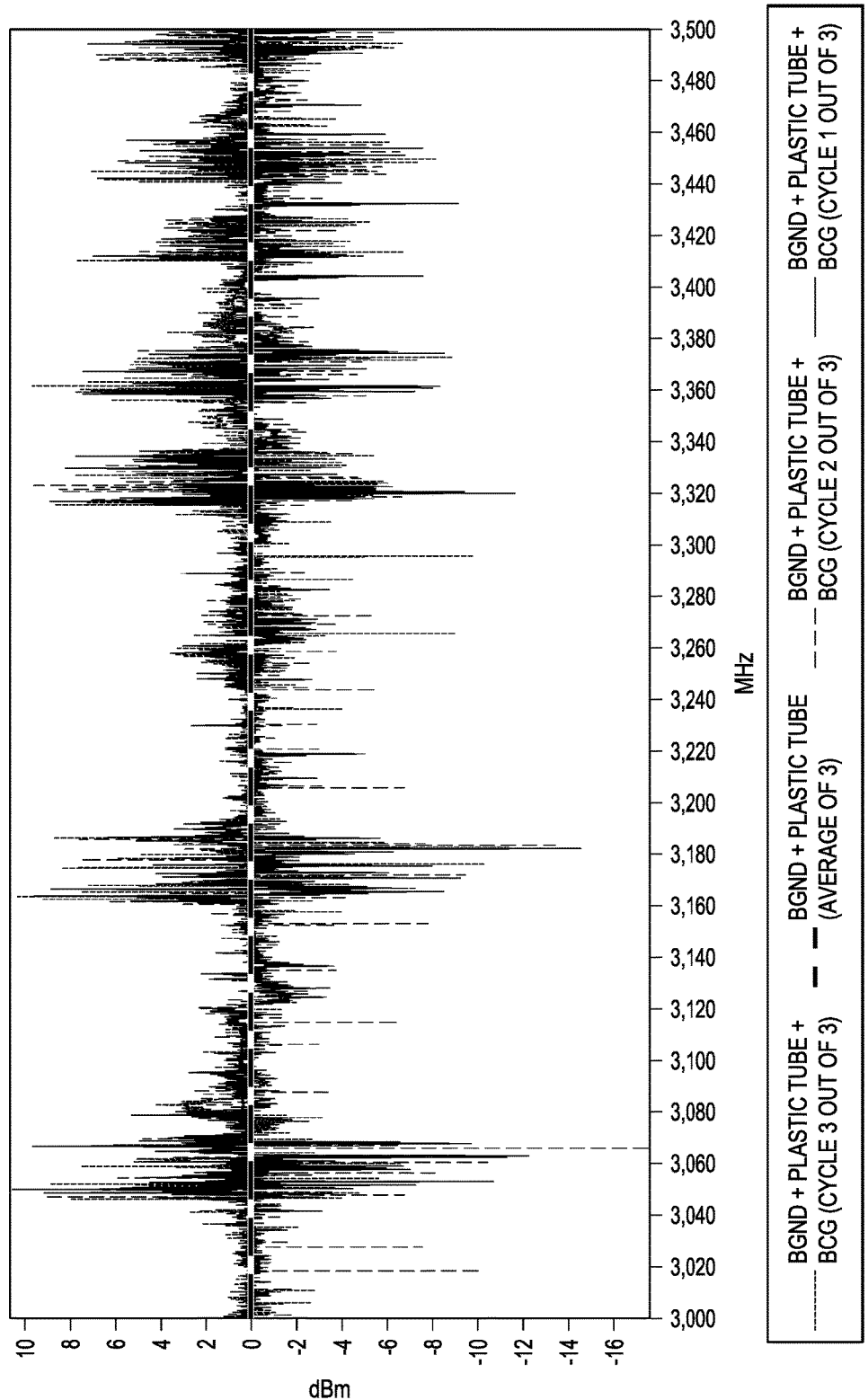
FIGS. 7A-7B illustrate example frequency spectra according to example embodiments.
Figure 7B:
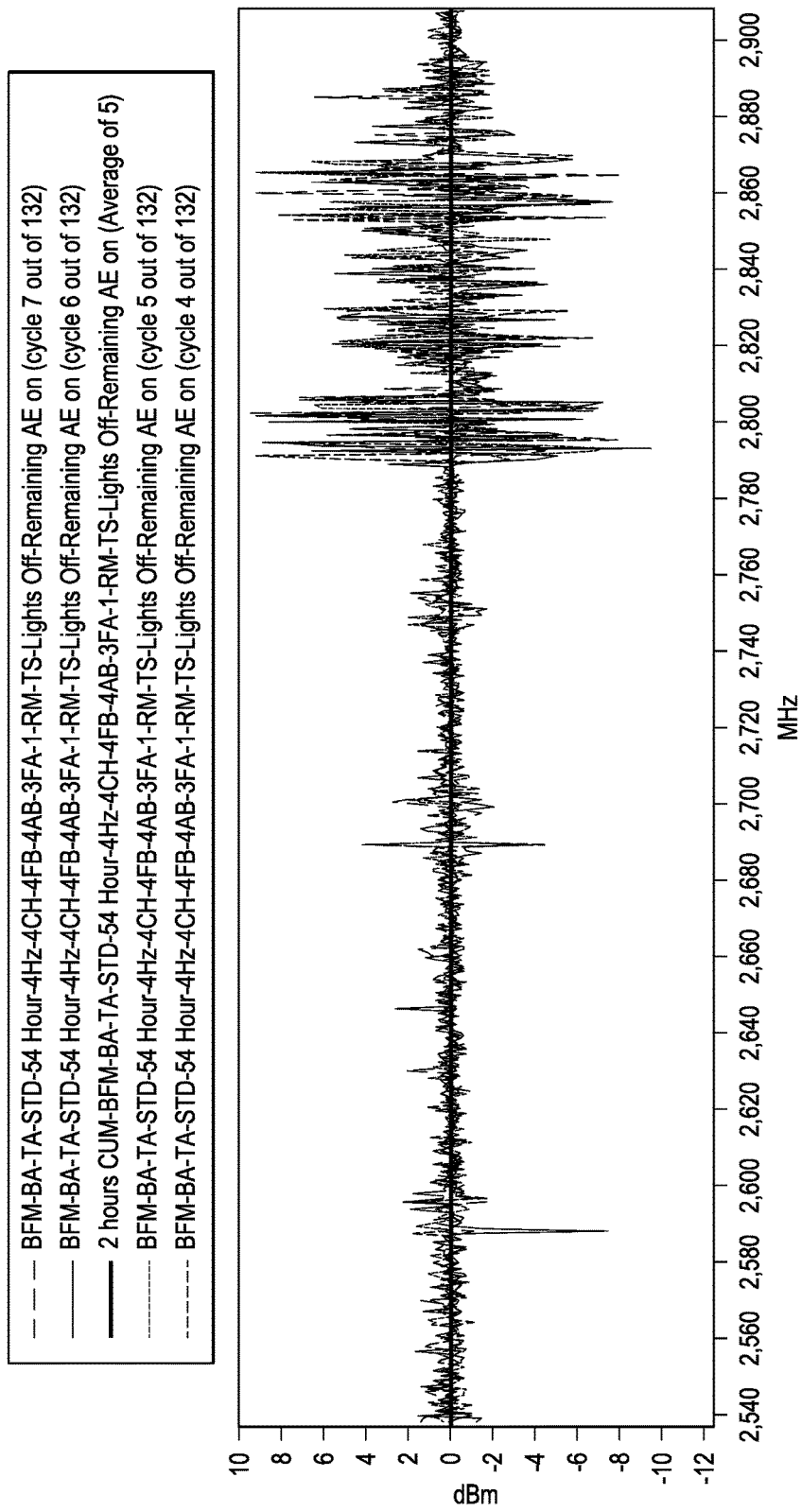
Figures 1, 7B:
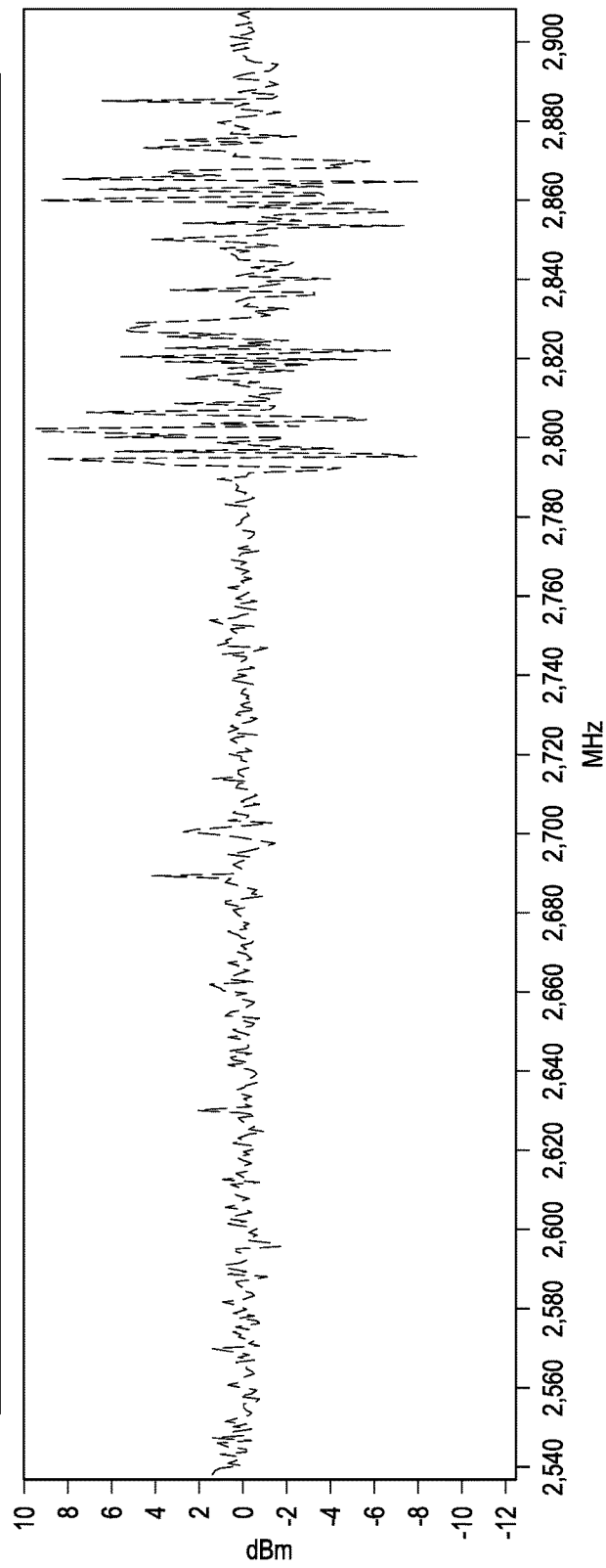
Figures 2, 7B:
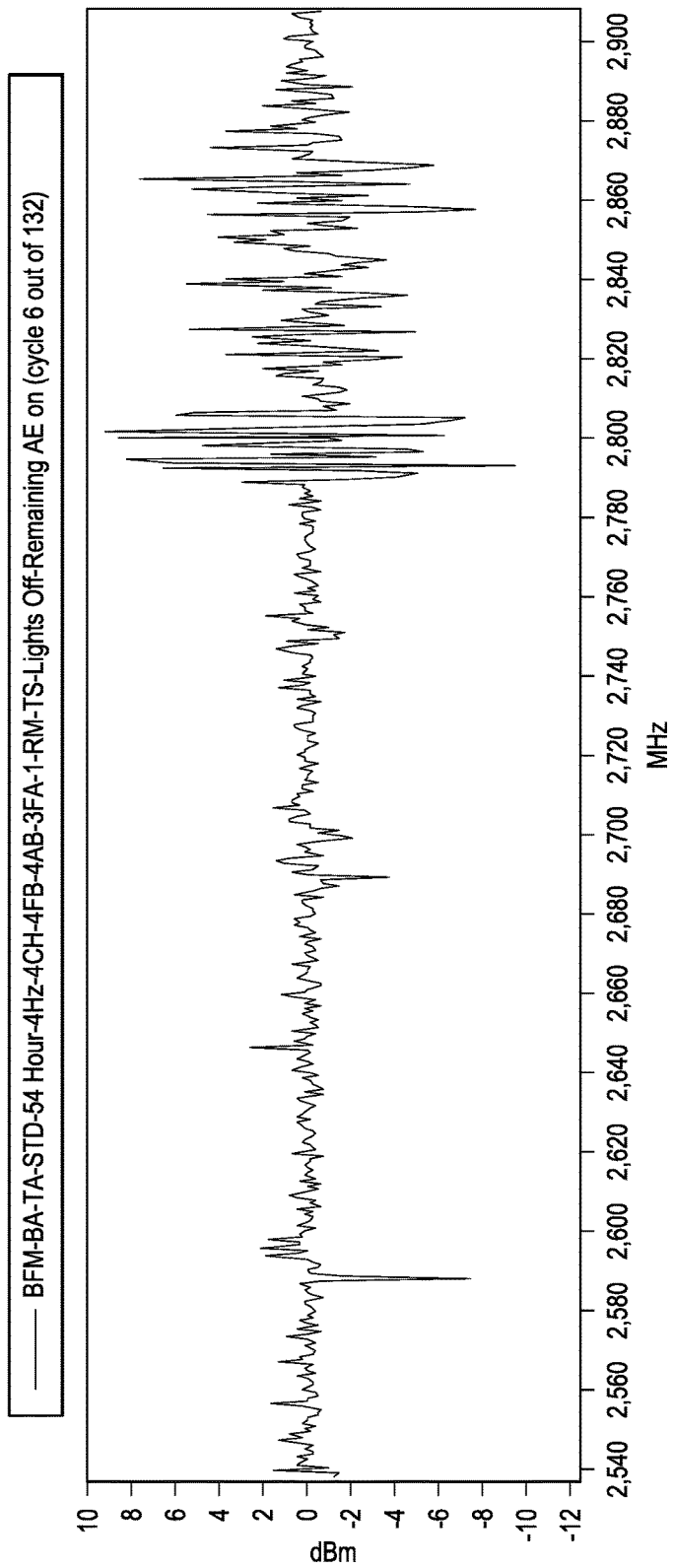
FIG. 2 illustrates a disease treatment system that may transmit multiple resonant frequencies according to an example embodiment of the disclosure.

As illustrated in FIGS. 2-5, the configuration of FIG. 1 may be altered in various ways within principle of the present disclosure. One of ordinary skill in the art would recognize similarities between various embodiments, therefore redundant discussions are omitted. FIG. 2, for example, illustrates disease treatment system 200 according to an example embodiment, where multiple resonant frequencies may be transmitted simultaneously to affect a particular disease condition. For illustration purposes, two sets of shielded containers 110 and 111—containing reference materials 112 and 113, respectively, which generate two distinctly different resonant frequency signals 120 and 121 respectively—and two sets of broadcast antenna boxes 130 and 131 are arranged in parallel in FIG. 2. Simultaneous processing and transmission of multiple resonant frequencies may impact target cells more effectively with accurate tuning while avoiding unnecessarily duplicative system components. For example, it is unnecessary to provide an additional signal generator or feedback antennae to induce the desired resonance from multiple signals. Multiple resonant frequencies may be identified in parallel through use of multiple source materials. Alternatively, resonant frequencies may be identified via calculation or trial-and-error. Captured resonant frequencies herein can be stored digitally or replicated by means of a suitable multi-frequency signal generator.

Figures 3, 7B:
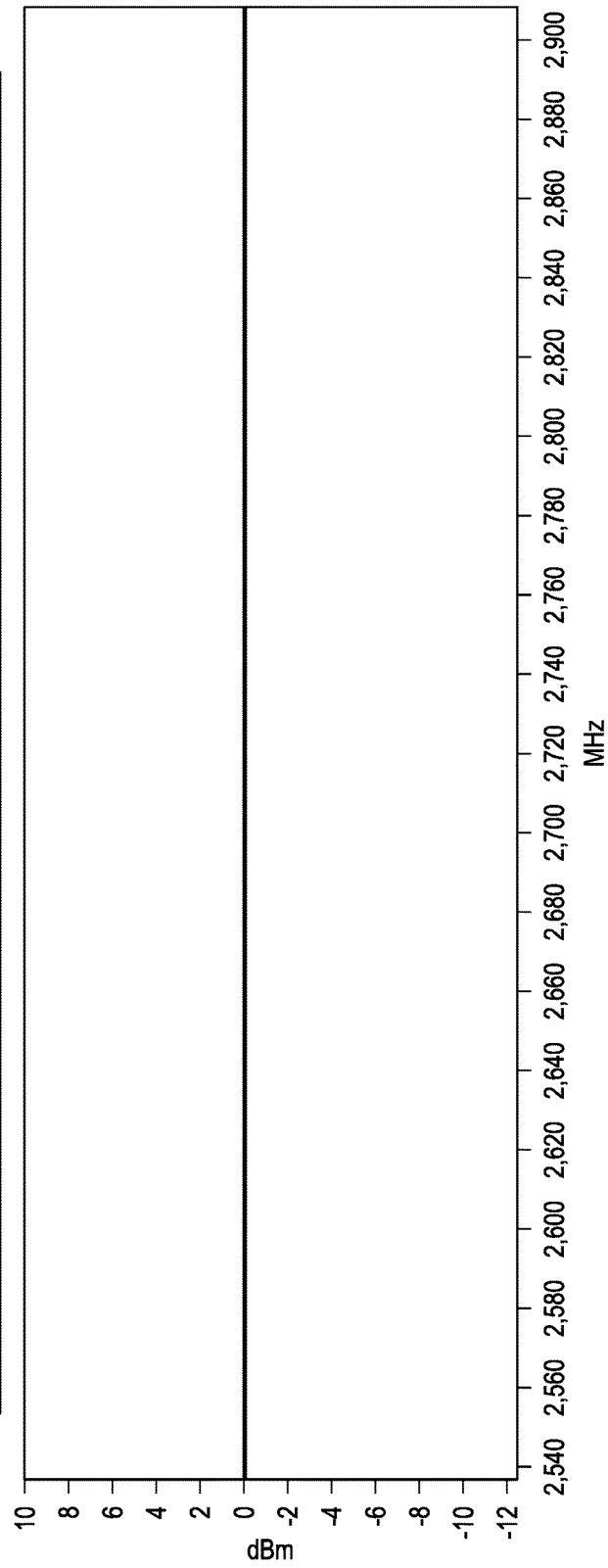
FIG. 3 illustrates a disease treatment system (comprising an amplifier) that may transmit a resonant frequency according to a specific example embodiment of the disclosure.

FIG. 3 illustrates disease treatment system 300 according to an example embodiment, which is similar to disease treatment system 100 except amplifier 171. In a positive feedback loop, amplifier 171 may situate between feedback antenna 170 and shielded container 110. Amplifier 171 may generate feedback signal 172, which helps amplify resonance that leads to the disruption of cellular homeostasis and induction of cell death.

Figures 4, 7B:
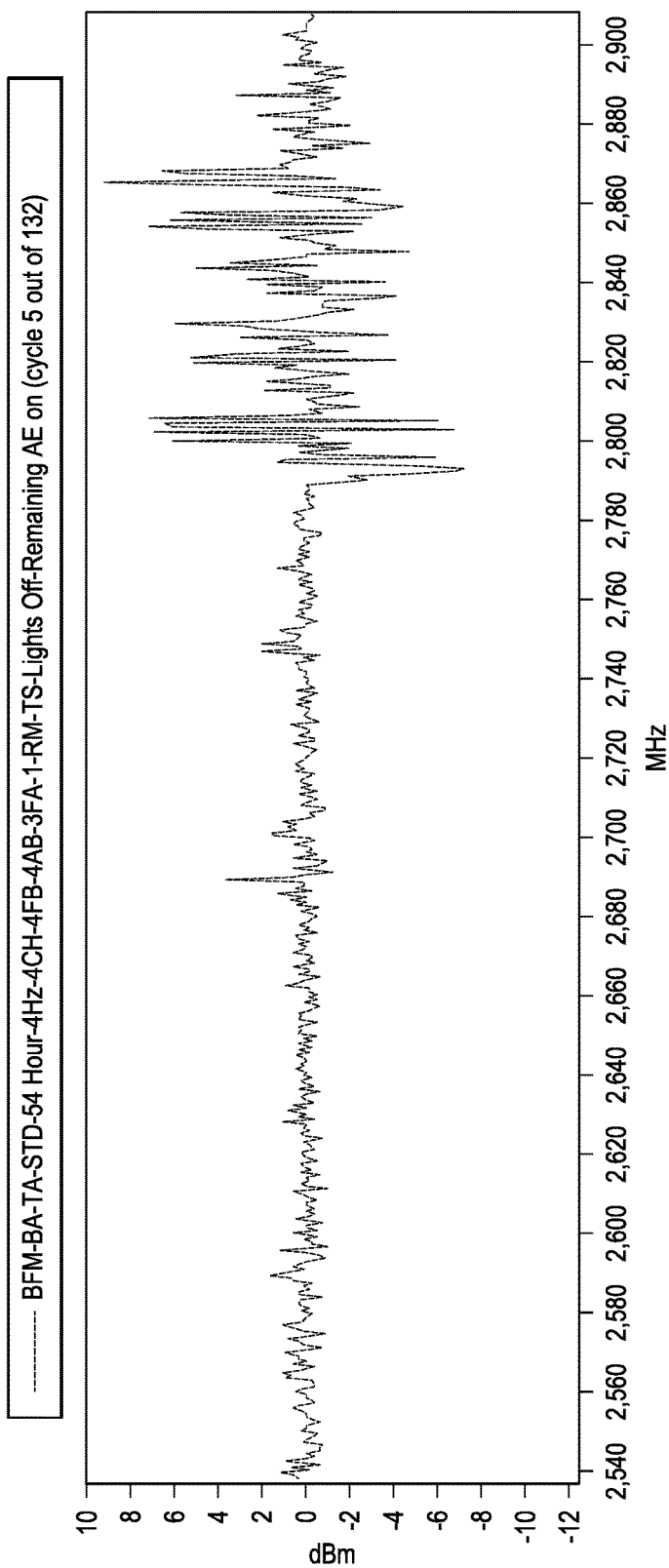
FIG. 4 illustrates a disease treatment system that may transmit a resonant frequency without a reference material according to a specific example embodiment of the disclosure.

FIG. 4 illustrates disease treatment system 400 according to an example embodiment, which removes the need for a reference material in each subsequent system used. Instead, resonant frequencies of one or more reference materials may be measured, captured, calculated, or otherwise determined off-site or beforehand in accordance with an example embodiment, and then recorded manually or digitized. Then, signal generator 410 may simultaneously generate digitized, calculated, captured, or measured frequencies of one or more reference materials. Signal generator 410 may be implemented as a multi-frequency signal generator or as multiple single-frequency signal generators. Broadcast antenna box 420 may comprise antennae 422 and 424 that work together. Antenna 422 may be implemented as a broadband antenna or as multiple single-frequency antennae, which receive(s) resonant frequency information from signal generator 410. Antenna 424 may be implemented as a broadband antenna, or as multiple single-frequency antennae for broadcasting resonance generating electromagnetic fields onto subject 140. Antenna 424 may simultaneous broadcast multiple resonant frequencies onto subject 140, which may impact target cells more effectively than other approaches such as transmitting different single-frequency signals consecutively. Feedback antenna provides a feedback signal back to antenna 424. A feedback loop may not be required with sufficient amplification via increased gain from signal generator 410 and/or via an external amplifier on the output of signal generator 410.

Figures 5, 7B:
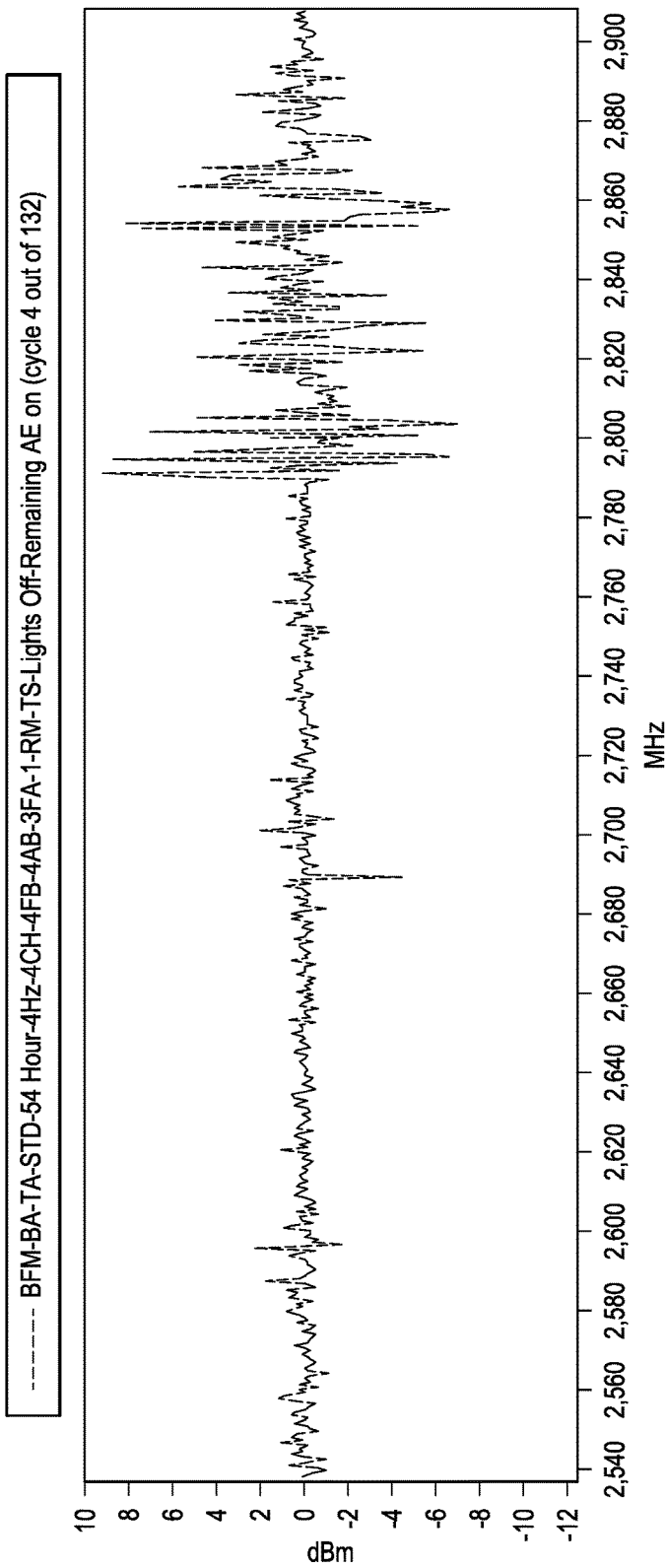
FIG. 5 illustrates a disease treatment system (comprising an amplifier) that may transmit multiple resonant frequencies according to an example embodiment of the disclosure.

FIG. 5 illustrates disease treatment system 500 according to an example embodiment, which is similar to disease treatment system 400 except amplifier 171. In a positive feedback loop, amplifier 171 may situate between feedback antenna 170 and antenna 524 to provide for necessary amplification of signals. Therefore, amplifier 171 sometimes removes the need for increased gain from signal generator 510 and/or external amplifier on the output of signal generator 510.

According to some embodiments, disease treatment systems may perform prolonged exposure of a subject carrying a disease that contains selected reference material(s) critical to its progression or survival. Exposure may be continuous or intermittent. Electromagnetic exposure induces amplified resonance within that critical component and stops a disease condition. In an example embodiment, exposing a subject to an electromagnetic field lasts continuously for a time period sufficient to cause death of cells or organisms related to the disease condition. Targeted electromagnetic radiation may be suitable for treating cancer, bacterial infections, viral infections, and other maladies.

Figure 6:
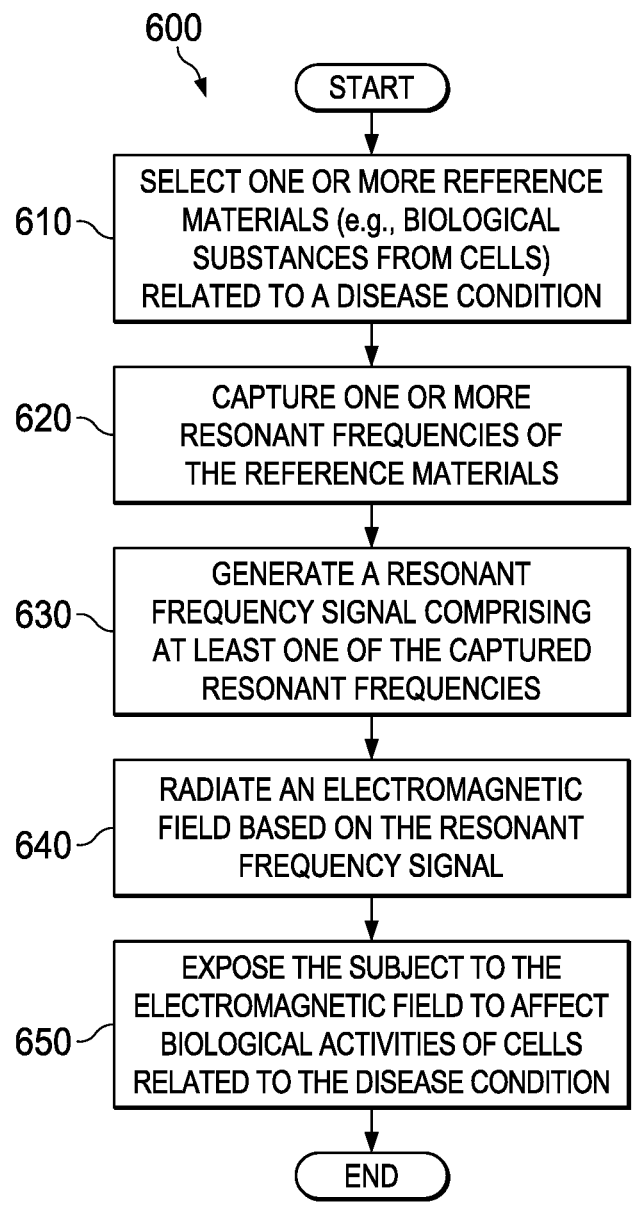
FIG. 6 illustrates a process for treating a disease condition with targeted electromagnetic radiation according to an example embodiment.

FIG. 6 is a flowchart showing process 600 for administering to a subject having or at risk of having a disease condition with resonance-based electromagnetic radiation, according to an example embodiment (e.g., system 100 as shown in FIG. 1). Process 600 may start in action 610, where one or more reference materials (e.g., reference material 112) related to the disease condition is selected. A reference material may be biological substances extracted from cells or other sources or may be synthetic substances (e.g., a synthesized peptide sequence or a synthetic DNA sequence). For example, the reference material may be key to the function, progression, viability, proliferation, continuation, and/or survival of the disease condition. In action 620, one or more resonant frequencies of reference materials are captured. In action 630, a resonance frequency signal (e.g., signal 120) is generated to carry at least one of the captured resonant frequencies. In action 640, a modulated broadband signal (e.g., signal 152) may be generated by a signal generator and provided to a first broadband antenna. In action 650, a booster signal (e.g., signal 154) comprising a single, low frequency waveform may be optionally generated by the signal generator and provided to a second broadband antenna. In action 660, an electromagnetic field (e.g., represented by signal 136 in FIG. 1) may be radiated or effectuated jointly based on the resonant frequency signal, the modulated broadband signal, and the booster signal (if present). In action 670, a subject (e.g., subject 140) having or at risk of having a target disease may be administered to by exposing the subject to the resonance generating electromagnetic field to affect biological activities of cells or organisms causing or associated with the disease condition.

As will be understood by those skilled in the art, various embodiments (including those involving additional steps) are contemplated in light of process 600. For example, in an example embodiment, a modulated broadband signal may be simultaneously modulated, in a signal generator, by at least a first waveform at a first frequency and at least a second waveform at a second frequency. The frequencies may be selected based on the application. For example the first frequency of the first waveform may be about 1 Hz or about 4 Hz, while the second frequency of the second waveform may be less than 1 MHz, less than 100 KHz (e.g., 2.2 KHz), etc.

Embodiments disclosed herein may treat a disease condition with targeted electromagnetic radiation from a suitable apparatus. Process of treatment may include selection and isolation of substances critical to the progression, viability, proliferation, continuation, and/or survival of a particular disease such as cancer, bacterial or viral infections and other maladies. A reference material may provide resonant frequencies (including harmonics) specific to that material which occur within the transmission bandwidth. Measurement and capture of the resonant frequencies may be performed for transmission and amplification of resonant frequency signals. Optionally, resonance may be amplified through a feedback loop, which may or may not include a source of additional amplification. An electromagnetic field developed in the near field zone of an antenna array may be tuned by means of the feedback loop.

FIG. 7A illustrates an example frequency spectrum, where multiple resonant frequencies are captured using Bacillus Calmette-Guerin (BCG), an attenuated strain of Mycobacterium bovis, as a reference material. Here, amplitude of an electromagnetic field is measured with a spectrum analyzer in peak hold mode during exposure of BCG cells through three cycles. The peak hold function fixes highest amplitude at every frequency during the scan in each selected bandwidth. The approximate areas of resonance can be better depicted by using SPAN32 software to subtract background radiation from each of the scans of the three cycles and graphing the results. Using this graphic as an example permits one to better visualize the resonant frequency trends. Precise determination of the applicable resonant frequencies may be obtained by an oscilloscope. As shown in FIG. 7A, the frequency spectrum of the electromagnetic field displays amplification at several resonant frequencies, such as those at about 3,000 MHz, 3,170 MHz, 3,330 MHz, 3,370 MHz, 3,410 MHz, 3,450 MHz, and 3,500 MHz. Some of these frequencies may be harmonic frequencies. One of ordinary skill in the art would recognize that a resonant frequency may actually be a representative frequency around which the electromagnetic spectra displays over time relatively higher amplitude and fluctuation than in those areas outside the frequencies of resonance.

Embodiments disclosed herein may be applied for treating a wide variety of disease conditions. An example cancer is Glioblastoma Multiforme (GBM), where selected reference materials may include hsa-miRNA-38; mutated alpha-kinase 2 gene; Hsp70 (70 kDa heat shock protein), CHI3L1 (chitinase-3-like protein 1), and/or the GBM cells themselves. Similar to the approach taken with BCG cells, spectral scans of exposed GBM cells were taken with a spectrum analyzer in the peak hold mode. In this particular case, however, the experiments were conducted inside of a Faraday room, thereby eliminating most background radiation. In order to depict the approximate areas of resonance, the spectral values of the scans conducted during the first two hours of exposure were averaged. By subtracting that average from consecutive scans on either side of the average, the resulting graphs, shown both individually and in composite form, permit visualization of the approximate areas of resonance related to the particular targets selected to treat GBM. Precise determination of actual resonant frequencies may be obtained by an oscilloscope. As shown in FIG. 7B, resonant frequencies for these combined selected reference materials within the electromagnetic spectra show increased amplification at certain frequencies such as about 2,795 MHz, 2,808 MHz, 2,820 MHz, 2,855 MHz, 2,860 MHz, and 2,865 MHz. These experiments produced a 30% reduction in GBM U-87 MG (a particular strain of GBM cancer chosen for the study) cell growth compared to a control group, which was the particular strain of GBM cancer chosen for the study.

Embodiments disclosed herein may also be applied for treating bacterial infections, such as *Mycobacterium Tuberculosis* (Mtb), where selected bacterial reference materials may include Phosphatidylmyo-inositol Mannosides (PIM), Arabinogalactan, Lipoarabinomannan (LAM), and Alpha-crystallin. Similarly resonant frequencies for these combined selected reference materials within the electromagnetic spectra displayed show increased amplification at various frequencies specific to the reference material. These in vitro experiments produced a 98% reduction in Mtb H37-RA bacterial cell growth compared to a control group which was the particular strain of Mtb chosen for the study.

Embodiments disclosed herein may also be applied for treating viral infections, such as Human Immunodeficiency Virus (HIV), where selected viral reference materials may include gp120, gp41, gp160, Gag polyprotein, Env protein, sequences of viral RNA, p24 protein, and/or pro-viral DNA. This in vitro experiment produced a 99% reduction in HIV-1 cell growth compared to a control group.

Embodiments disclosed herein may treat a wide variety of disease conditions, which are not exhaustively listed herein. For example, the efficacy of a device with respect to Glioblastoma may be applied effectively for other diseases such as neurodegenerative disorders (e.g. Niemann Pick).

More specific example embodiments based on experimental studies are illustrated in FIGS. 8-13 to show that non-invasive electromagnetic field technologies have a significant inhibitory effect on the proliferation of various cells, such as glioblastoma for treating GBM (type U-87 MG) cells in culture, which relate to the treatment of GBM. Experimental studies observe the cellular and molecular responses of U-87 glioblastoma cells to the effects of utilizing a tunable, non-ionizing radiation technology that is unlikely to induce the serious side effects commonly observed with chemotherapy. Broadband (RF or low microwave) electromagnetic field is tuned by means of proprietary oscillating waveforms (either 1 Hz or 4 Hz), selected reference materials and a positive feedback loop. By targeting specific cancer molecules (e.g., oligonucleotides and proteins) that contribute to cancer cell proliferation in glioblastoma with this technology, continuous exposure of cells for 54 hours (h) resulted in the inhibition of cell growth (e.g., by about 30%) with concurrent cell death (apoptosis). The effects of a treatment system on cells in culture did not appear to act on molecular processes common to temozolomide or docetaxol treatment, thus acting by novel non-cytotoxic mechanism. This technology has the potential to be customized for individual tumors and may contribute to the emerging strategy of personalized medicine.

Disclosed herein are embodiments of non-invasive technologies, which employ non-ionizing, self-tuned, electromagnetic (EM) radiations that can be added to therapeutic armamentarium for GBM, alone or in combination with standard therapies. In example embodiments, first reference materials reflecting critical components of the target cells may be selected. The system then amplifies the resonant frequencies of the reference materials. These resonances are transmitted to the target cells which alter the behavior of corresponding reference molecules in target cells, inducing mitotic arrest and cell death.

A treatment system used in experiments may emit, for example, an ultra-low intensity (−50 to −90 dBm), broadband (100 MHz-3.5 GHz) electromagnetic radiation. Using an array of reference antennae and transceivers coupled to a waveform generator, a treatment system produces a non-propagating electromagnetic field in a near-field zone of the antennae. A field may be self-tuned by means of oscillating waveforms (e.g., at 1 Hz [slow] or 4 Hz [fast] or other frequency) to capture a resonant frequency and harmonics of selected reference materials. Prescribed reference material resonances may then be amplified within a positive feedback loop, leading to the disruption of cellular homeostasis and induction of cell death. Targeted molecules may be selected by identifying critical oncogenic or tumor suppressive processes in tumors.

Reference materials may then be isolated, prepared, stabilized, and used to target primary glioblastomas (as modeled in experiments further outlined below). The resonance generating electromagnetic fields technology can also be customized for individual tumors. Unlike ionizing radiation, some disclosed embodiments employ non-ionizing, ultra-low power electromagnetic radiation, which is not associated with significant side effects. Thus, the present disclosure offers a novel method of therapy with minimal side effects that will be part of the emerging personalized medicine approach to combating diseases.

Figure 8:
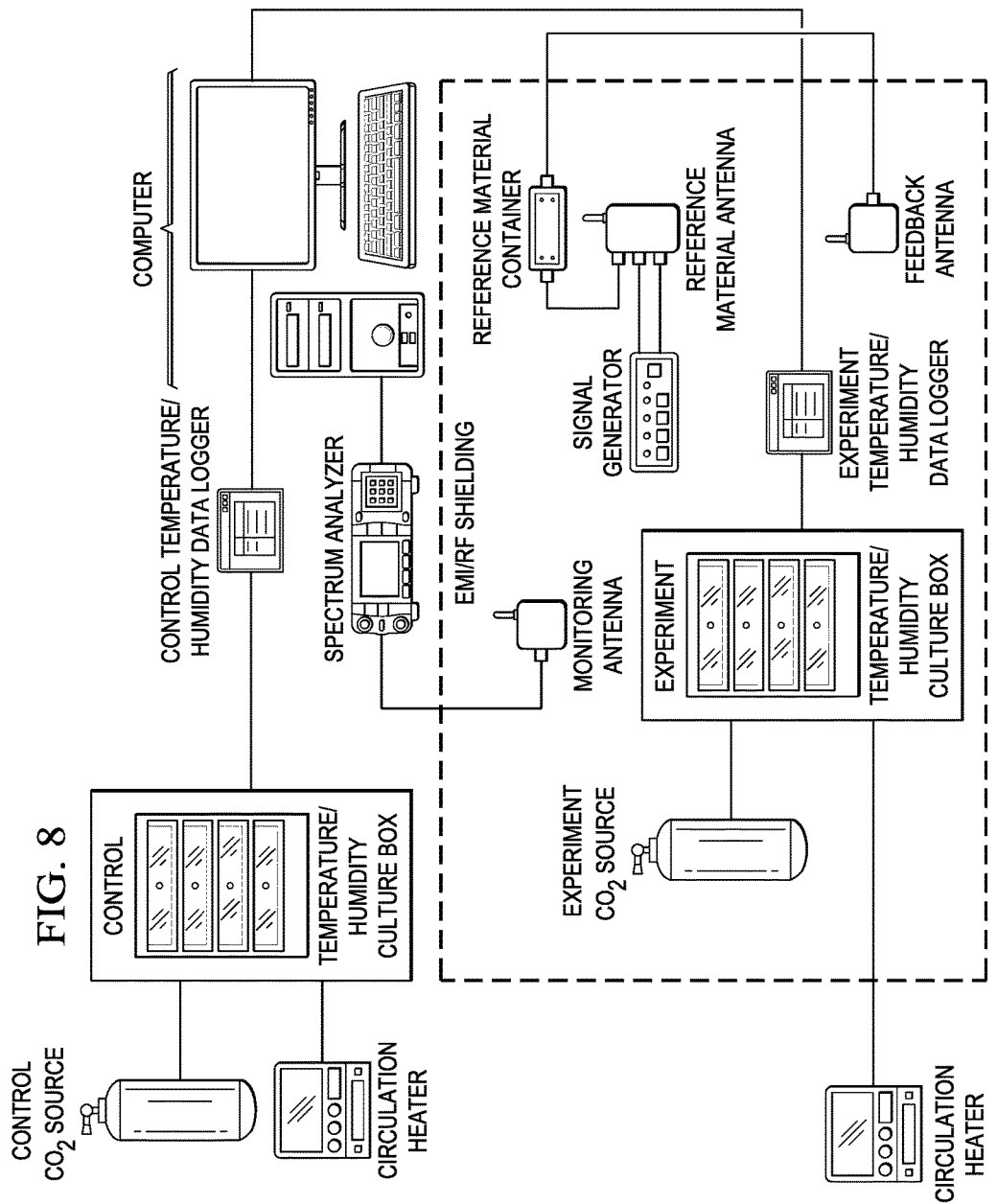
FIG. 8 illustrates an example experimental setup according to an example embodiment.

FIG. 8 illustrates an experimental system according to some embodiments. In experiments, to minimize inadvertent exposure of laboratory personnel to the electromagnetic fields generated during these experiments, an apparatus may be placed in an electromagnetic interference/RF shielding Faraday room (sized 3.2 m×2.5 m×2.5 m). This shielding provides an attenuation of 100 dB to electric fields and plane waves from 14 KHz to 10 GHz and 50 dB to magnetic fields at 14 KHz rising to 90 dB at 200 KHz (tested in accordance with IEEE-STD-299).

Custom-designed culture boxes may be assembled entirely from acrylic to prevent interference with electromagnetic fields associated with metal shelves and other components. Temperature/humidity readings inside culture boxes may be recorded on a continuous basis (e.g., 60 second intervals) using Ethernet data recorders, and incubator temperatures may be controlled using individual circulating heaters for each incubator. Appropriate carbon dioxide (CO2) levels are maintained by a continuous flow (e.g., 2.8 standard cubic feet per hour) of a gas mixture (e.g., 5% CO2 and 95% air) via a rotometer. An identical experimental setup may be established in a second laboratory over 30 meters away from the Faraday room to serve as an unexposed control for experiments.

Reference materials that may be selected include hsa-miRNA-381; mutated alpha-kinase 2 gene; Hsp70 (70 kDa heat shock protein) and CHI3L1 (chitinase-3-like protein 1). DNA and RNA oligonucleotides may be synthesized and purified by high performance liquid chromatography (HPLC). Oligonucleotides may be solubilized, their volumes reduced, and then transferred to an appropriate container for stabilization. Hsa-miR-381-5p (MIMAT0022862) sequence is 5'-AGCGAGGUUGCCCUUUGUAUAU-3'. This microRNA is highly expressed in brain tumors and may play a major role in glioma progression by targeting and inactivating LRRC4 (leucine-rich repeat C4), a tumor suppressor gene that is specifically expressed in brain. Targeting this microRNA in U-87 MG cells may significantly inhibit cell viability, proliferation, and upregulate expression of tumor suppressor LRRC4.

A U-87 MG cell line may have a homozygous mutated alpha-kinase 2 gene (hg18:uc002lhj.2, uc002lhk.1) with a 15 bp section 5'-AGGACACATCAACTG-3' deleted from the gene on the coding strand. A DNA oligonucleotide 5'-AGGGAGACTG^TTACCATTGC-3' may contain ten bp of an alpha-kinase 2 coding sequence flanking the deletion site. Recombinant proteins may solubilize in a PBS buffer. A buffer may be exchanged, with volume reduced, and then transferred to an appropriate container for stabilization.

Heat shock proteins may be expressed in all cells and may be more highly expressed in cancer cells due to the protection needed from the stress of their high metabolic requirements. In U-87 MG, a human recombinant protein interacts with ATF5, an activating transcription factor, and stabilizes the protein from degradation. In other cancers, a human recombinant protein may protect anti-apoptotic proteins while suppressing pro-apoptotic activity. Targeting a human recombinant protein may sensitize U-87 MG to chemical and oxidative stress, radiation therapy, as well as reduce stability of certain survival proteins. This reference material may also be stabilized.

Chitinase-3-like protein 1 is a secreted glycoprotein that is overexpressed in glioblastomas, and is highly overexpressed in U-87 MG cells. This protein is pro-angiogenic, contributes to radio resistance and tumor progression in glioblastomas. Targeting another human recombinant protein CHI3L1 may decrease proliferation and metastasis in U-87 MG cells. This reference material may also be stabilized.

To ensure proper operation of a disease treatment system, in some embodiments an electromagnetic field intensity within a Faraday Room may be measured continuously using a spectrum analyzer with a frequency range between 9 kHz and 3.5 GHz via a higher order proprietary antenna. During initial system calibration, spectral readings, e.g., via proprietary software, may be taken outside of the Faraday Room. Background radiation intensity outside of the Faraday Room typically ranged between −60 and −90 dBm.

After sealing the room, the following baseline scans may be taken to confirm that performance of the Faraday room is in good order. Electric field strength inside the Faraday room with the equipment operating may average approximately 0.003 V/m. This level is far below the guidelines issued for safe exposure to the general public. An increase in field intensity of approximately 15 to 20 dBm above unshielded background radiation can be measured across the full 3.5 GHz span. When software confirms that a latest scan indicates greater than 90% correlation level with a prior immediate scan (adequate tuning), cultures containing U-87 MG cells may be inserted into a treatment culture box. Field intensity can be further increased by 15 to 20 dBm in areas of resonance. The changes in field intensity may confirm that a system is operating properly.

Figure 9:
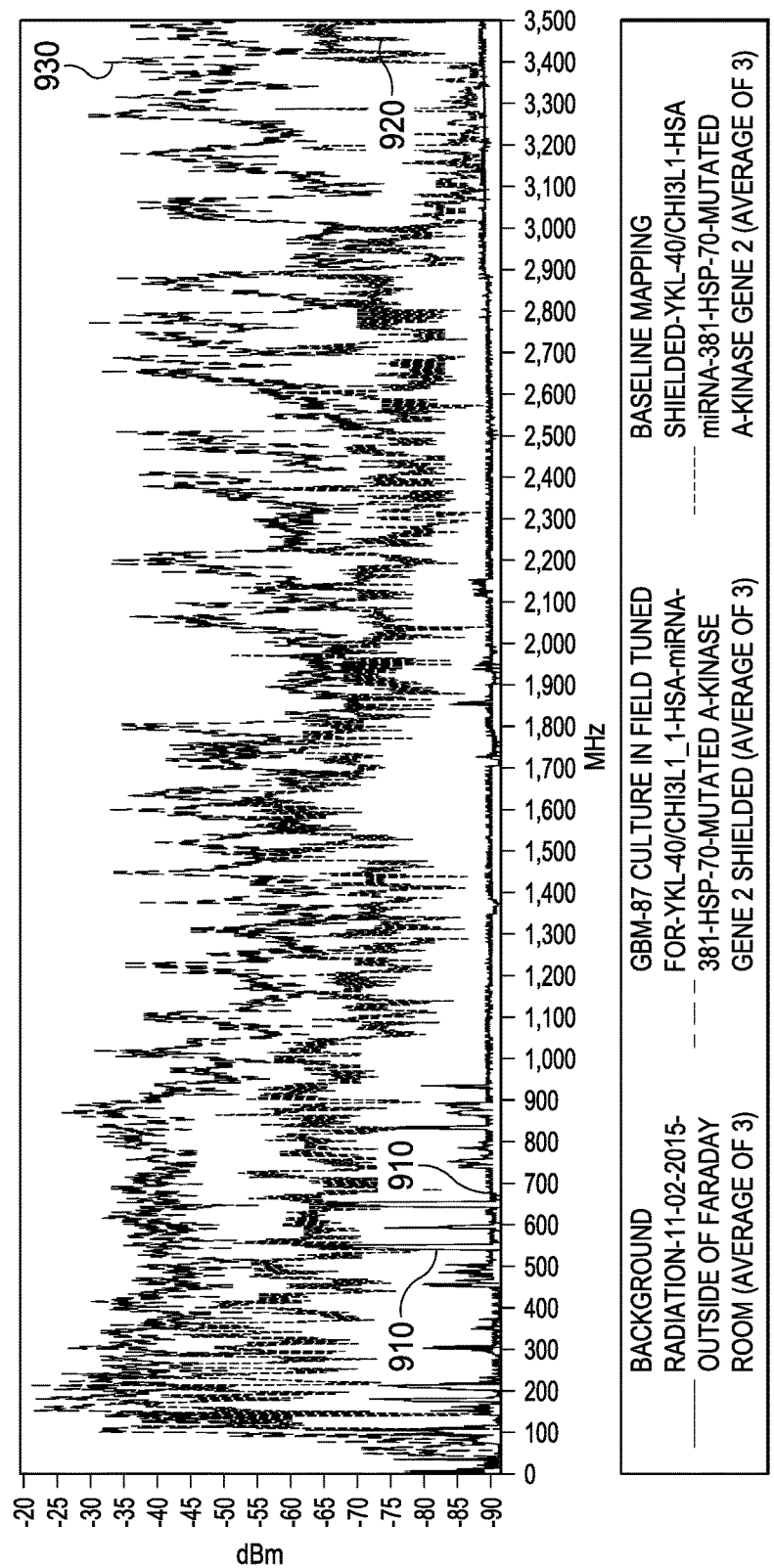
FIG. 9 illustrates an example comparison of three spectral field strengths according to an example embodiment.

FIG. 9 illustrates an example comparison of three spectral field strengths: (910) the spectra of unshielded background radiation; (920) the spectra once a field has been tuned for four selected macromolecules before U-87 MG cultures are introduced to the field; and (930) the spectra after U-87 MG cultures are brought into the tuned field.

By continuously measuring the broadband spectra of an electromagnetic field, proper operation of a treatment system may be confirmed, which also facilitates observation and analysis of changes in areas showing enhanced resonance response and spectral correlation percentages during the entire 54 hour period of exposure for each iteration of study.

U87-MG cells may be grown in minimal essential media containing 10% fetal bovine serum (FBS) and 1 mM sodium pyruvate. U87-MG cells may be routinely passaged weekly at a density of 5000 cells/cm2 with media changes every three or four days, and maintained in a humidified 5% CO2 incubator at 37° C.

U-87 MG cells may be plated at a density of $4 \times 10^5$ cells/100-mm dish. 24 hours after seeding, plates may be randomized to the treatment culture box inside the Faraday room and exposed to a resonance generating field, or to the control culture box outside the Faraday room, to serve as the unexposed control. Cells may be exposed to slow modulation (1 Hz) or fast modulation (4 Hz) resonance generating electromagnetic field for 54 hours continuously. At the end of exposure, half of the dishes may be processed and those respective cells may be harvested by trypsinization, and an aliquot of live/unfixed cells may be used to determine cell number, PS externalization, and caspase-3/7 activity using a cell analyzer as described below. Remaining cells may be fixed for cell cycle analysis and DNA fragmentation analysis as described below. Control cells may be cultured under identical conditions. Remaining dishes may be maintained for a further 96 hour outside the Faraday room, in a $CO_2$ incubator, and then processed in a manner similar to that described above.

U-87 MG cells may be plated at a density of $8 \times 10^5$ cells/150-mm dish. 48 hours after plating, cells may be treated with vehicle control or 25 nM docetaxel for 72 hours. At the end of treatment, cells may be harvested by trypsinization, and an aliquot of live/unfixed cells may be used to determine cell number, PS externalization, and caspase-3/7 activity using a cell analyzer. Remaining cells may be fixed for cell cycle analysis using a cell analyzer and DNA fragmentation analysis by BD LSRII Flow Cytometry as described below.

U-87 MG cells harvested by trypsinization may be pooled with media plus washes and pelleted by centrifugation. The cells may be re-suspended in complete media diluted 1:10 with PBS (1% FBS/PBS). For determination of count and viability, an aliquot of the cell suspension may be diluted 1:10 with a count & viability reagent, which differentially stains viable and non-viable cells based on their permeability to two DNA binding dyes, and incubated for 5 minutes in the dark at room temperature according to manufacturer's protocol. For detection of phosphatidylserine (PS) externalization, an aliquot of cell suspension appropriately diluted in 1% FBS/PBS may be mixed 1:1 with an Annexin V & dead cell reagent and incubated for 20 minutes in the dark at room temperature according to manufacturer's protocol. The Annexin V & dead cell reagent utilizes Annexin V to detect PS on the external membrane of apoptotic cells. The dead cell marker 7-AAD, which is normally excluded from healthy and early apoptotic cells, may be used as an indicator of cell membrane integrity. To assay caspase-3/7 activity, an aliquot of cell suspension appropriately diluted in 1% FBS/PBS may be mixed with caspase-3/7 reagent and incubated for 30 minutes in the dark at 37° C. according to manufacturer's protocol. The caspase-3/7 reagent is a cell membrane permeable DNA binding dye that is linked to DEVD peptide substrate.

Cleavage by active caspase-3/7 releases the dye within the cell and results in translocation to the nucleus, binding to DNA and high fluorescence. For cell cycle analysis, an ethanol-fixed cell suspension may be obtained by taking an aliquot of cell suspension, pelleting by centrifugation, resuspending in PBS, and fixing in 70% ethanol at −20° C. Fixed cells may be washed in PBS/0.2% BSA, pelleted by centrifugation, resuspended in a cell cycle reagent, and incubated for 30 minutes in the dark at room temperature according to manufacturer's protocol. A cell cycle reagent may be a proprietary formulation containing the DNA intercalating dye propidium iodide and RNAse A. The multiparametric fluorescent detection of individual cells may be performed by a cell analyzer, a microcapillary flow cytometer equipped with a 532-nm laser, a forward scatter and two fluorescence (YLW 576/26, RED 680/30) detectors. Data acquisition and analysis of count & viability, Annexin V & dead cell, and caspase-3/7 assays may be done by analysis software. Post-acquisition analysis of cell cycle data may be performed using software (e.g., FlowJo 7.6.5).

For analysis of DNA fragmentation, U-87 MG cells may be harvested by trypsinization, collected by centrifugation, fixed in 2% formaldehyde in PBS, and permeabilized in 70% EtOH at −20° C. DNA strand breaks in cells undergoing apoptosis may be indirectly labeled with bromodeoxyuridine by terminal transferase and detected by FITC-conjugated monoclonal antibody to bromodeoxyuridine using the APO-BRDU kit according to manufacturer's protocol. Cells may be counterstained with 5 µg/ml propidium iodide containing RNase A for detection of total DNA, and two-color analysis of DNA strand breaks and cell cycle may be achieved by flow cytometry. Flow cytometric analysis may be performed on a BD LSR II Flow Cytometer equipped with three excitation lasers (405-nm, 488-nm and 633-nm). For DNA fragmentation analysis, FITC and PI signals may be collected by 488-nm octagon detection array with no color compensation. 10,000 events gated on single cell populations may be collected and post-acquisition analysis may be performed using software FlowJo 7.6.5.

Figure 10A:
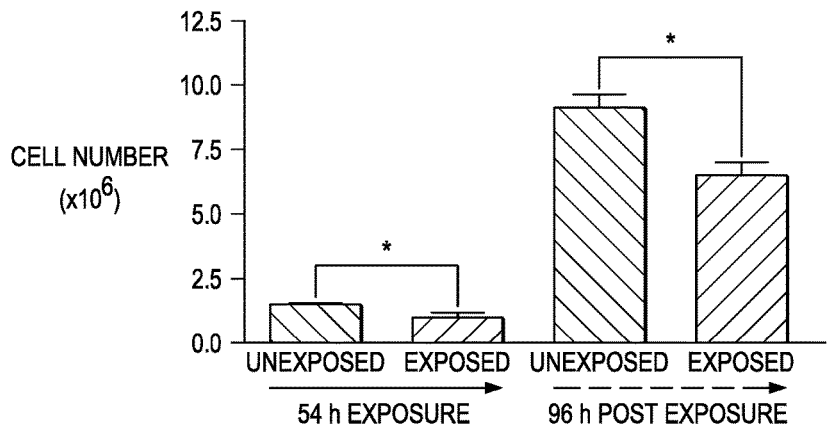
FIGS. 10A-10E illustrate comparisons of changes in control cells versus exposed cells at slow modulation for the U-87 MG strain of GBM, according to an example embodiment.
Figure 10B:
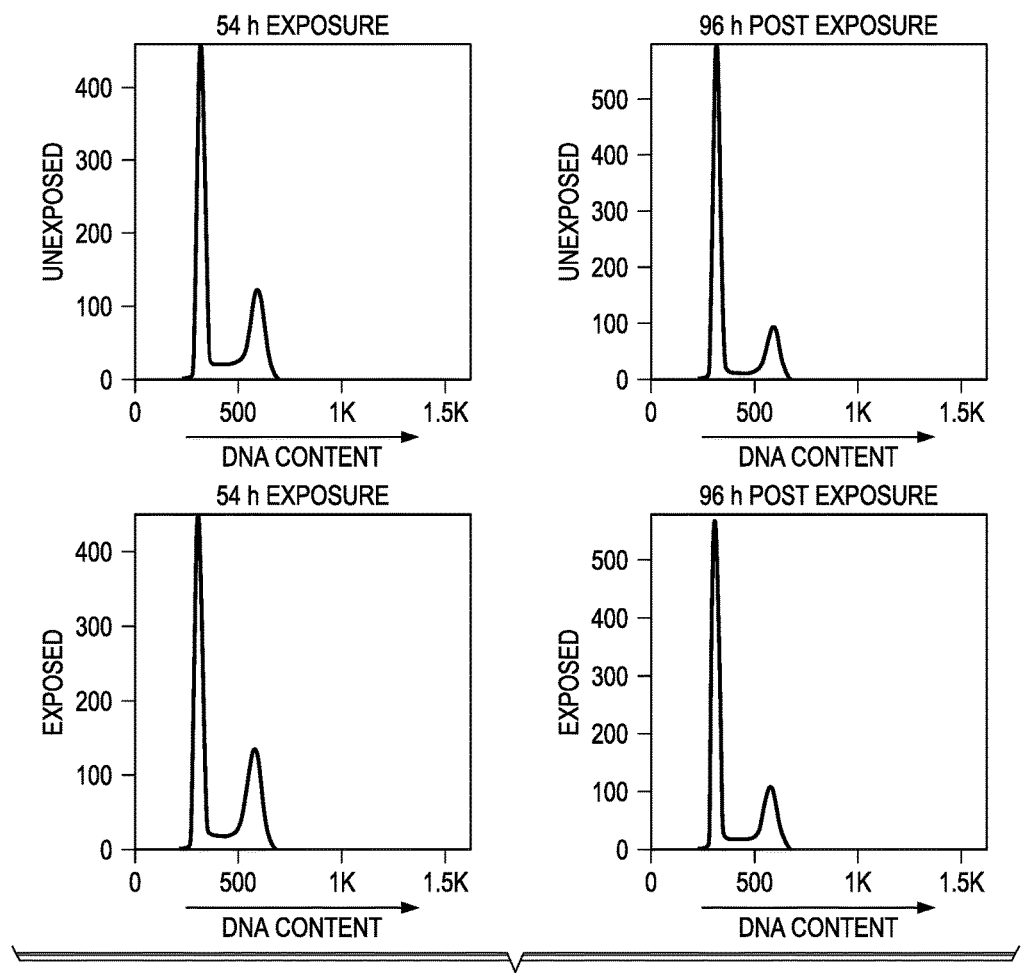
Figure 10C:
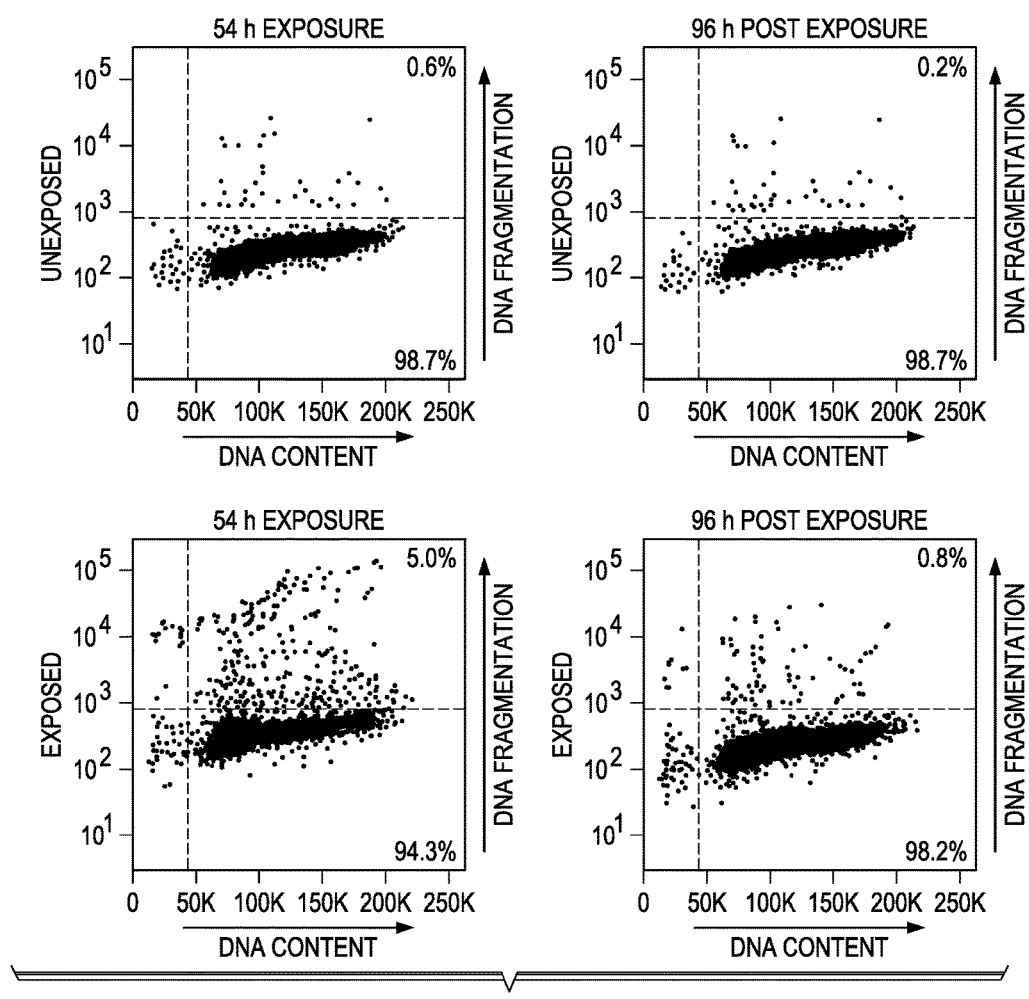
Figure 10D:
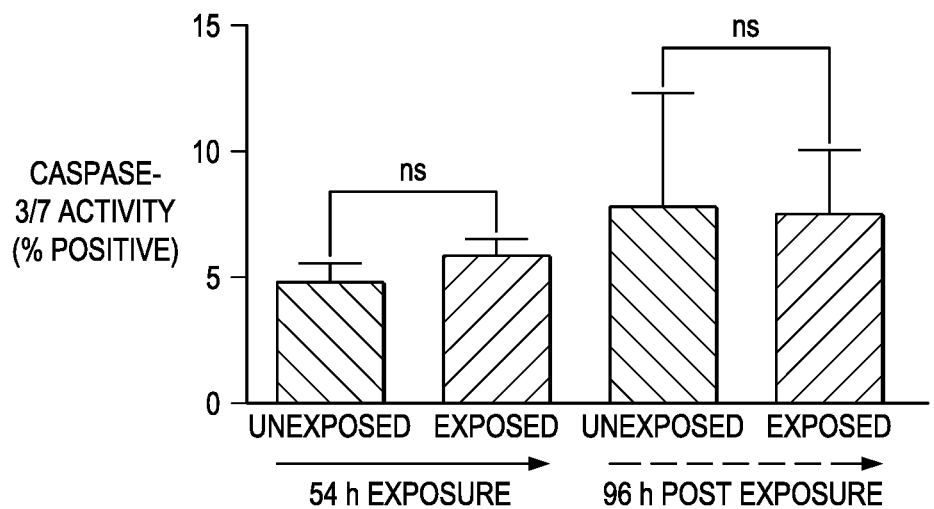
Figure 10E:
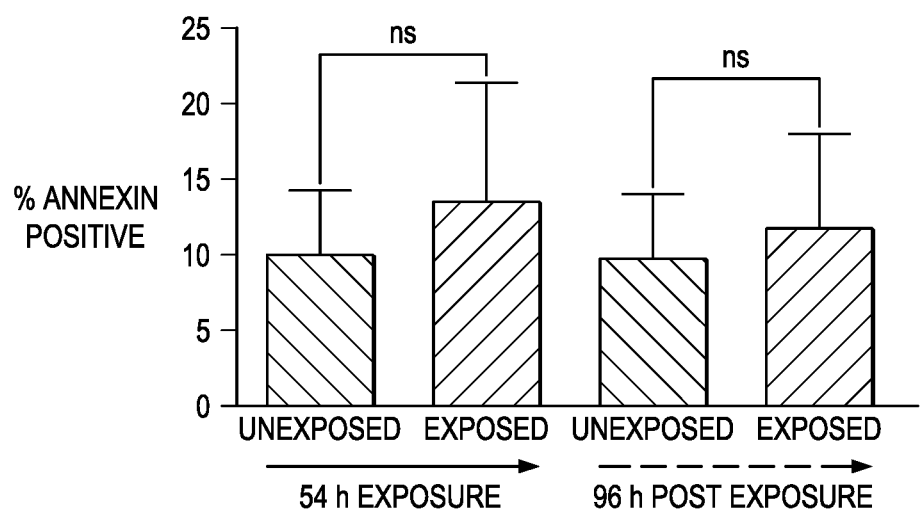

FIGS. 10A-10E illustrate comparisons of changes in control cells versus cells exposed at slow modulation for the U-87 MG strain of GBM. Specifically, FIG. 10A shows changes in U-87 MG cell number; FIG. 10B shows changes in U-87 MG cell cycle, including the sub G0 population; FIG. 10C shows changes in DNA fragmentation in U-87 MG in all four quadrants of the histogram; FIG. 10D shows changes in caspase-3/7 activation; and FIG. 10E shows changes in phosphotidylserine (PS) as measured by Annexin V staining. Data are represented as Mean±SD of three independent biological experiments (*$p<0.1$; ns—not significant).

After 54 hours' exposure to a resonance generating field, there may be a significant decrease of 30% in U-87 MG cell number ($1.0 \times 10^6$ cells/dish), relative to unexposed control cells ($1.5 \times 10^6$ cells/dish), as shown in FIG. 10A. After the cells are removed from the irradiated area, cell growth rate may be restored, although at 96 hours' post exposure, the cell number of exposed cells ($6.3 \times 10^6$ cells/dish) still lag 31% behind that of the unexposed cells ($9.1 \times 10^6$ cells/dish). These imply that resonance generating electromagnetic fields, tuned to the four references materials outlined above, may arrest cell growth as long as the cells are in the field. Cell growth may be restored in the absence of continued exposure.

Exposure of U-87 MG cells to slow modulation resonance generating electromagnetic fields also induces a significant and apparently sustained change in cell cycle kinetics compared to unexposed controls, as shown in FIG. 10B and Table 1.

Table 1 shows cell cycle analysis of U-87 MG cells after exposure to resonance generating electromagnetic fields at slow modulation. At the end of 54 hours exposure or 96 hours post exposure, cells may be harvested and cell cycle may be determined by incubating the cells in a cell cycle reagent, following the manufacturer's protocol. Data represent the Mean±SD of three independent biological replicates (*$p<0.1$).

TABLE 1

|  | Sub-$G_0$ | G1 | S | G2/M |
| --- | --- | --- | --- | --- |
|  | 54 hour exposure | | | |
| unexposed | 0.5 ± 0.4 | 51.5 ± 1.0 | 19.7 ± 1.0 | 28.5 ± 1.3 |
| exposed | 0.6 ± 0.6 | 49.7 ± 0.4* | 16.8 ± 2.4 | 33.1 ± 2.5* |

TABLE 1-continued

|  | Sub-$G_0$ | G1 | S | G2/M |
|---|---|---|---|---|
|  | 96 hour post exposure | | | |
| unexposed | 0.7 ± 0.7 | 59.7 ± 4.7 | 14.4 ± 3.5 | 24.7 ± 1.7 |
| exposed | 0.8 ± 0.4 | 52.7 ± 2.4* | 18.3 ± 2.9 | 27.6 ± 1.3* |

A decrease in cell number shown in FIG. 10A may be accompanied by a significant decrease in the proportion of the cells in the G1 phase of the cell cycle and a concomitant significant increase in the proportion of cells in G2/M. Redistribution of cells in a cell cycle may be maintained even in cells 96 hours post-exposure, suggesting that resonance generating electromagnetic fields under slow modulation have an extended effect on cell cycle kinetics, even though cell number increases once cells are removed from the field. This somewhat paradoxical effect may be explained by the induction of cell death, as measured by DNA fragmentation, as shown in FIG. 10C and Table 2, which show that resonance generating electromagnetic fields induce a large increase in TUNEL positive cells after 54 hours of exposure. 96 hours post exposure, DNA fragmentation may have returned to the levels seen in unexposed cells.

Table 2 shows analysis of DNA fragmentation of U-87 MG cells after exposure to resonance generating electromagnetic fields at slow modulation. At the end of 54 hour exposure or 96 hour post exposure, cells may be harvested, fixed in PBS, and permeabilized. DNA fragmentation may be determined by flow cytometry. Data show percentage of the cell population with DNA fragmentation in all four quadrants of the histogram and represent the Mean±SD of three independent biological replicates (*p<0.1).

TABLE 2

|  | DNA Frag (+) Apoptotic bodies (upper left quadrant) | DNA Frag (+) Cells (upper right quadrant) | DNA Frag (−) Cells (lower right quadrant) | DNA Frag (−) Apoptotic bodies (lower left quadrant) |
|---|---|---|---|---|
|  | 54 hour exposure | | | |
| unexposed | 0.03 ± 0.01 | 0.97 ± 0.41 | 98.5 ± 0.25 | 0.53 ± 0.28 |
| exposed | 0.05 ± 0.03 | 4.09 ± 2.79 | 95.5 ± 3.0 | 0.39 ± 0.16 |
|  | 96 hour post exposure | | | |
| unexposed | 0.03 ± 0.01 | 0.41 ± 0.29 | 98.7 ± 0.03 | 0.81 ± 0.29 |
| exposed | 0.07 ± 0.04 | 1.14 ± 0.86 | 98.0 ± 0.74 | 0.81 ± 0.17 |

Analysis of apoptosis using two additional markers of apoptosis-caspase-3/7 activation (FIG. 10D), a marker of the early stages of apoptosis, and Annexin V staining of phosphytidylserine on the outer leaflet of the dying cell and a marker of the later stages of apoptosis (FIG. 10E), suggest that neither of common apoptotic processes is involved in the induction of cell death by resonance generating electromagnetic fields. It is also possible that the apoptotic events are sufficiently asynchronous that the population of cells expressing these markers never reach significance relative to the background levels of cell death in the control cultures.

U-87 MG cells in separate experiments may be exposed to a resonance generating electromagnetic field for 54 hours continuously at fast modulation, the results from which are shown in FIG. 11, Table 3, and Table 4.

Figure 11A:
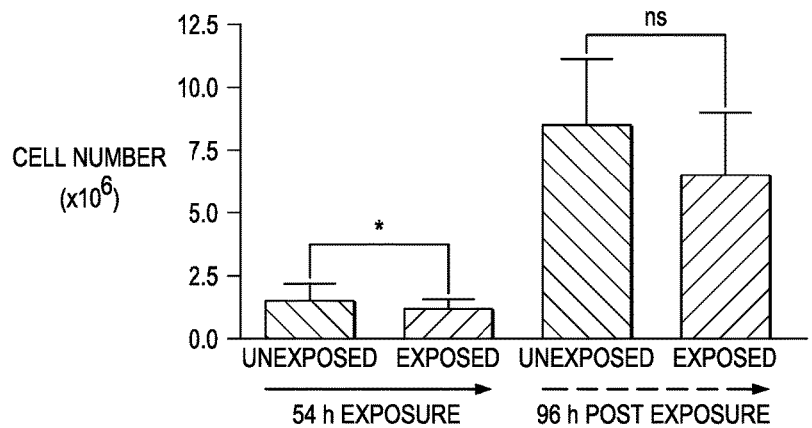
FIGS. 11A-11E illustrate an analysis of U-87 MG strain of GBM cells proliferation and apoptosis after exposure to resonance generating electromagnetic fields at fast modulation, according to an example embodiment.
Figure 11B:
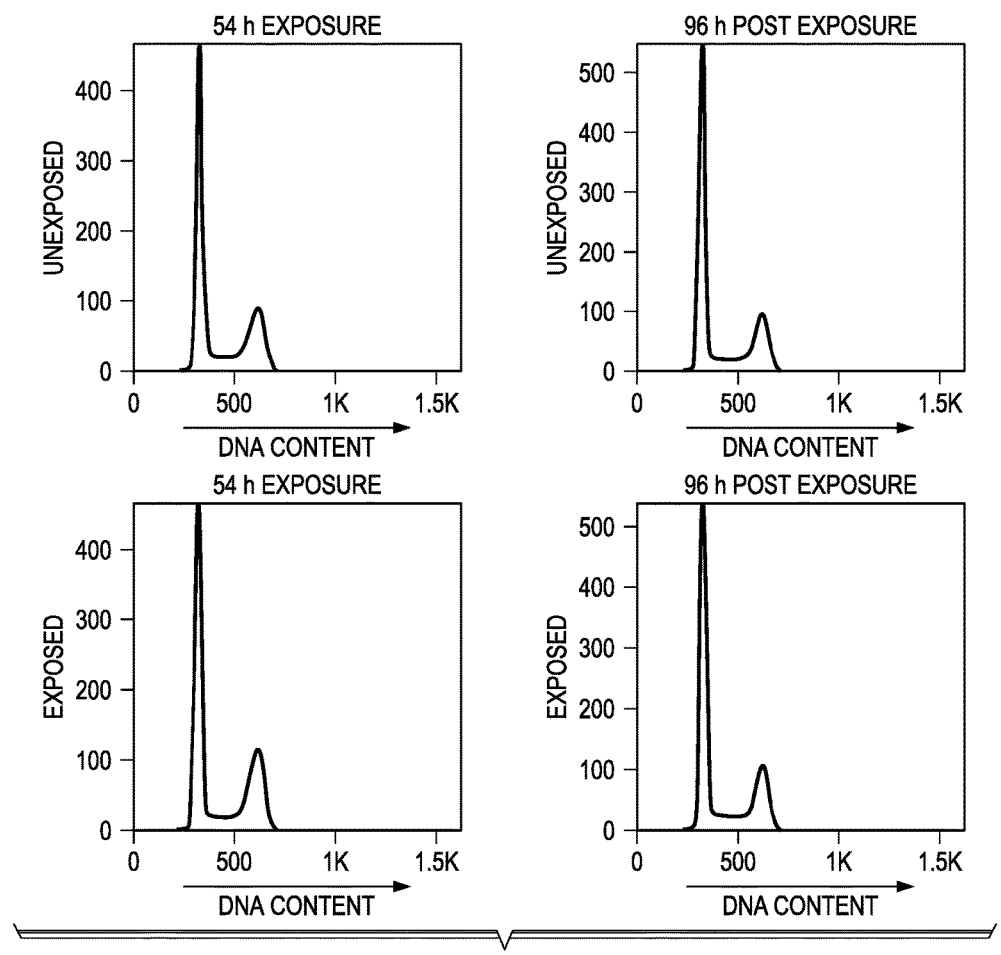
Figure 11C:
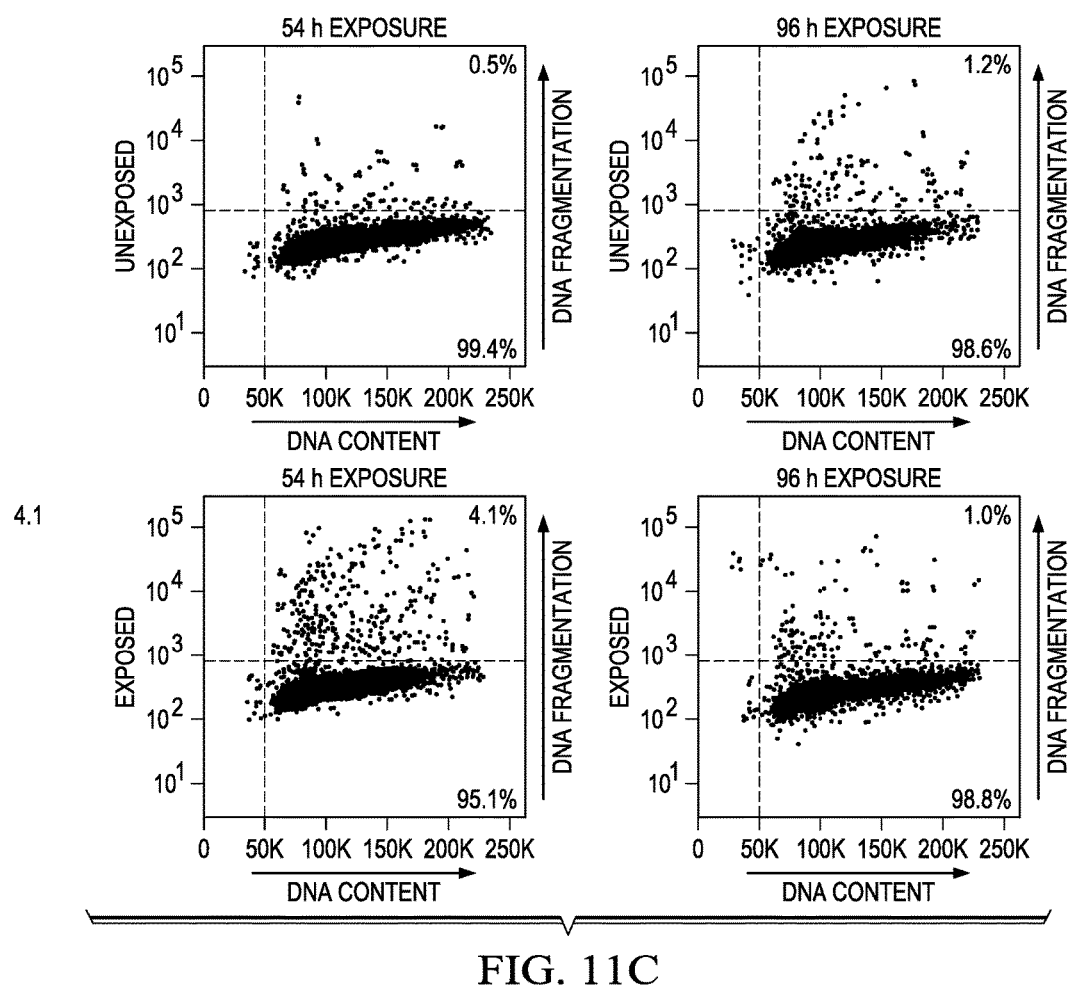
Figure 11D:
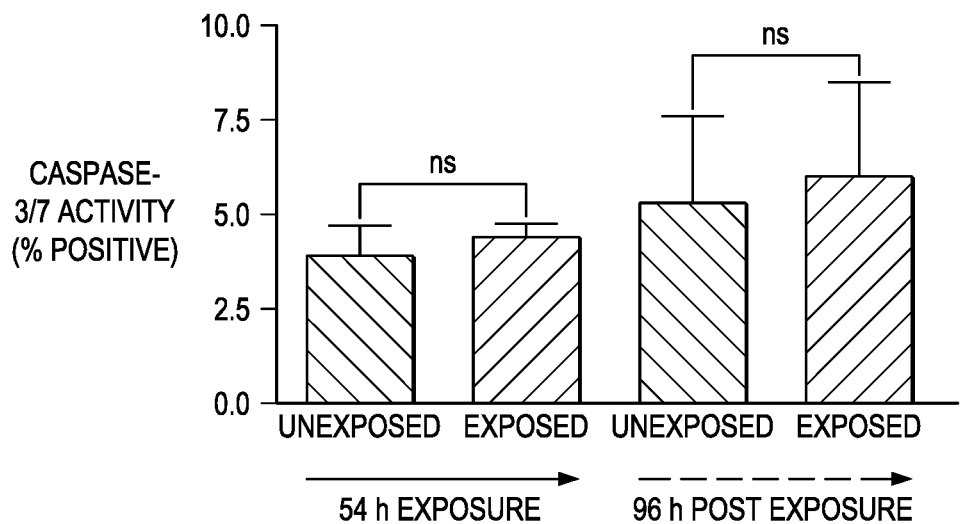
Figure 11E:
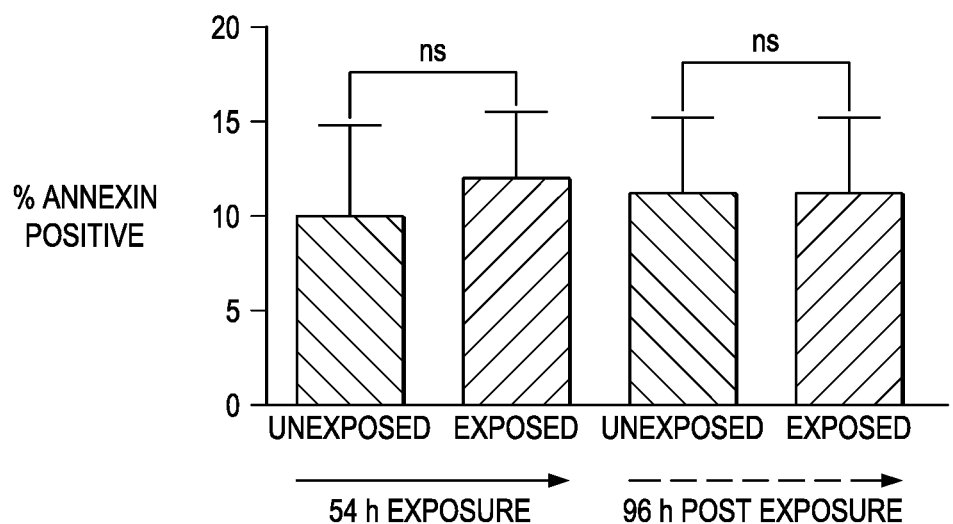

FIGS. 11A-11E represent an analysis of U-87 MG cells proliferation and apoptosis after exposure to resonance generating electromagnetic fields at fast modulation. FIGS. 11 A-E show comparisons of changes in control cells versus exposed cells. Specifically, FIG. 11A shows changes in U-87 MG cell number; FIG. 11B shows changes in U-87 MG cell cycle, including the sub G0 population; FIG. 11C shows changes in DNA fragmentation in U-87 MG in all four quadrants of the histogram; FIG. 11A shows changes in caspase-3/7 activation; and FIG. 11A shows changes in PS as measured by Annexin V staining. Data are represented as Mean±SD of four independent biological experiments (*p<0.1; ns—not significant).

Table 3 is a cell cycle analysis of U-87 MG cells after exposure to resonance generating electromagnetic fields at fast modulation. At the end of 54 hour exposure or 96 hour post exposure, cells may be harvested and cell cycle may be determined by incubating the cells in a cell cycle reagent, following the manufacturer's protocol. Data represent the mean±SD of four independent biological replicates (*p<0.1).

TABLE 3

|  | Sub-$G_0$ | G1 | S | G2/M |
|---|---|---|---|---|
|  | 54 hour exposure | | | |
| unexposed | 0.2 ± 0.3 | 52.9 ± 3.5 | 16.3 ± 4.1 | 30.7 ± 7.3 |
| exposed | 0.6 ± 0.3* | 49.4 ± 3.9 | 16.9 ± 2.4 | 32.8 ± 5.1 |
|  | 96 hour post exposure | | | |
| unexposed | 0.5 ± 0.5 | 55.1 ± 5.8 | 15.6 ± 3.5 | 28.5 ± 7.4 |
| exposed | 0.4 ± 0.3 | 52.8 ± 3.8 | 16.7 ± 4.2 | 29.5 ± 5.6 |

Table 4 is an analysis of DNA fragmentation of U-87 MG cells after to resonance generating electromagnetic fields at fast modulation. At the end of 54 hour exposure or 96 hour post exposure, cells may be harvested, fixed in PBS, and permeabilized. DNA fragmentation may be determined by flow cytometry. Data show percentage of the cell population with DNA fragmentation in all four quadrants of the histogram and represent the mean±SD of four independent biological replicates (*p<0.1).

TABLE 4

|  | DNA Frag (+) Apoptotic bodies (upper left quadrant) | DNA Frag (+) Cells (upper right quadrant) | DNA Frag (−) Cells (lower right quadrant) | DNA Frag (−) Apoptotic bodies (lower left quadrant) |
|---|---|---|---|---|
|  | 54 hour exposure | | | |
| unexposed | 0.02 ± 0.03 | 0.6 ± 0.29 | 99.2 ± 0.34 | 0.24 ± 0.07 |
| exposed | 0.04 ± 0.02 | 3.99 ± 1.76* | 95.7 ± 1.73* | 0.28 ± 0.06 |
|  | 96 hour post exposure | | | |
| unexposed | 0.03 ± 0.02 | 1.26 ± 0.84 | 98.1 ± 0.89 | 0.65 ± 0.30 |
| exposed | 0.04 ± 0.05 | 2.01 ± 1.93 | 97.3 ± 1.96 | 0.64 ± 0.31 |

To compare resonance generating electromagnetic fields with the well characterized effects of chemotherapeutic drugs, U87 cells may be treated with 25 nM docetaxel for 72 hours. At this dose and concentration docetaxel has been shown to be as effective as temozolomide in arresting cell growth in U-87 MG cells. Docetaxel decreases U-87 MG cell number by approximately 20%, although this effect does not reach significance over the 72 h time course. This effect is accompanied by a significant decrease in the proportion of the cells in G1 along with significant increases in the proportion of cells in S phase and also in the sub G0 population, as shown in FIG. 12B and Table 5. The increase in the sub G0 population does not appear to be accompanied by a significant increase in DNA fragmentation, as shown in FIG. 12D and Table 5), but is associated with a significant increase in caspase-3/7 activation and Annexin V positive cells, as shown in FIGS. 12D-E.

Figure 12A:
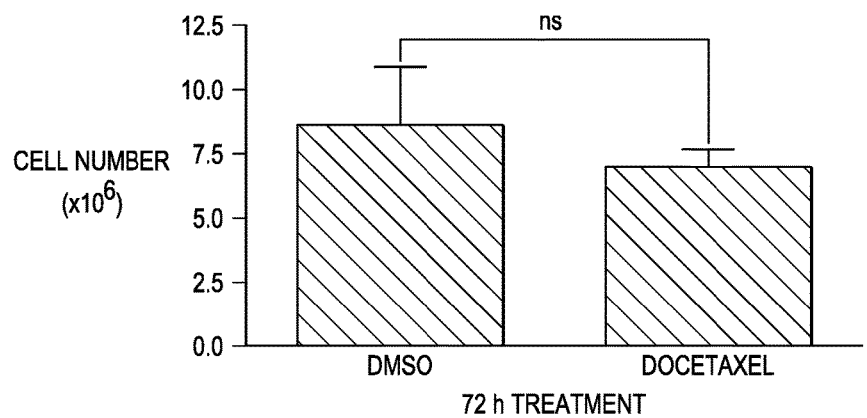
FIGS. 12A-12E illustrate an analysis of the U-87 MG strain of GBM cells proliferation and apoptosis after 72 hours treatment with 25 nM docetaxel.
Figure 12B:
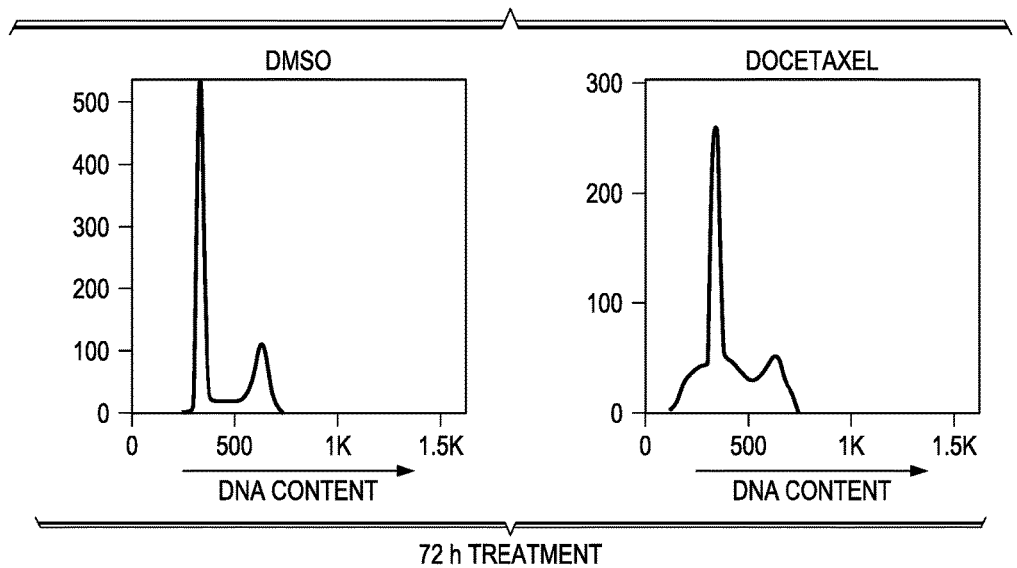
Figure 12C:
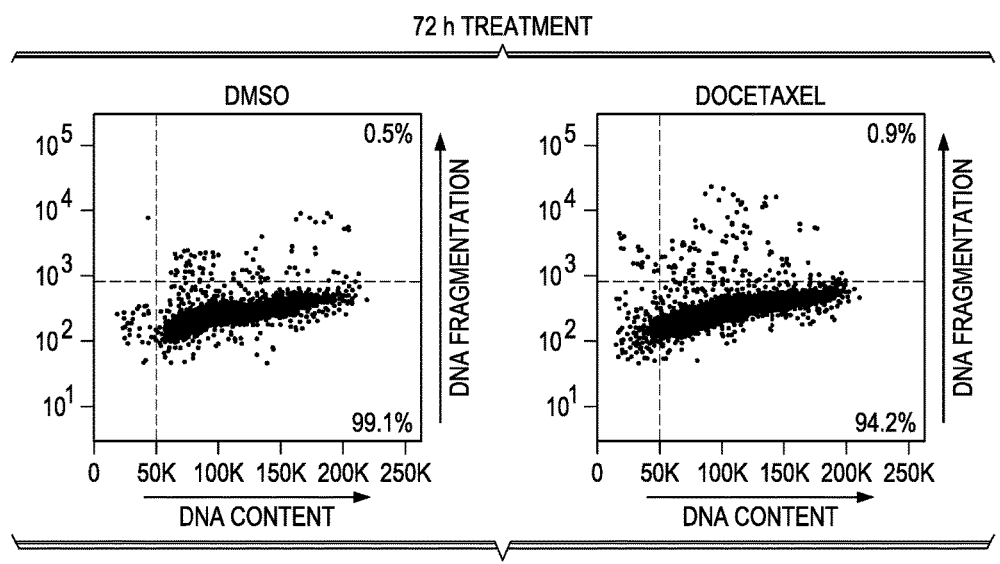
Figure 12D:
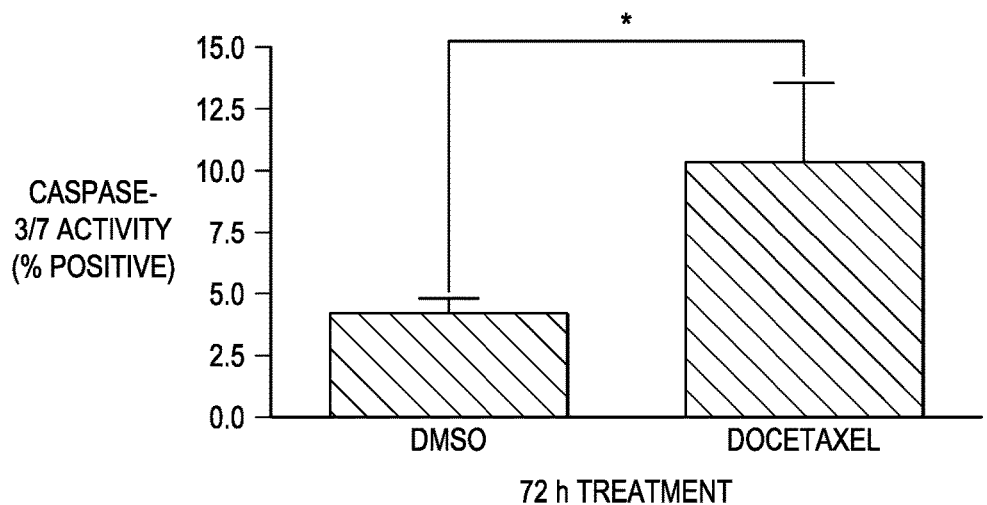
Figure 12E:
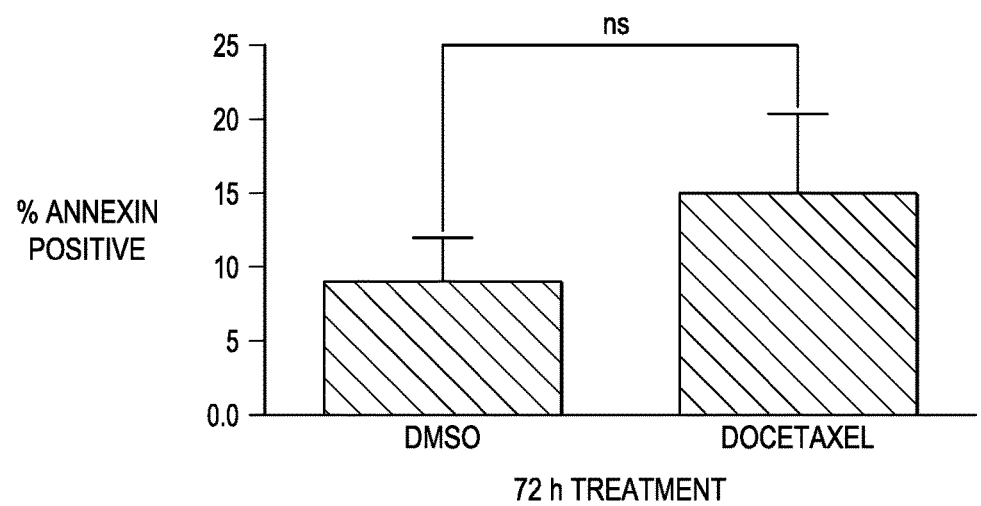

FIGS. 12A-12E are an analysis of U-87 MG cells proliferation and apoptosis after 72 hour treatment with 25 nM docetaxel. FIGS. 12 A-E show comparisons of changes in U-87 MG cell number in the absence and presence of 25 nM docetaxel. Specifically, FIG. 12A shows changes in U-87 MG cell number; FIG. 12B shows changes in U-87 MG cell cycle, including the sub G0 population; FIG. 12C shows changes in DNA fragmentation in U-87 MG in all four quadrants of the histogram; FIG. 12D shows changes in caspase-3/7 activation; and FIG. 12B shows changes in PS as measured by Annexin V staining. Data are represented as Mean±SD of three independent biological experiments (*$p<0.1$; ns—not significant) with the exception of DNA Fragmentation which had only two independent biological experiments.

Table 5 is a cell cycle analysis of U-87 MG cells after 72 hour treatment with 25 nM docetaxel. At the end of 72 hour treatment, cells may be harvested and cell cycle may be determined by incubating the cells in a cell cycle reagent and following the manufacturer's protocol. Data represent the mean±SD of three independent biological replicates (*$p<0.1$).

TABLE 5

|  | 72 hour treatment | | | |
| --- | --- | --- | --- | --- |
|  | Sub-$G_0$ | G1 | S | G2/M |
| DMSO | 0.6 ± 0.3 | 53.0 ± 5.8 | 14.2 ± 2.4 | 31.8 ± 7.1 |
| Docetaxel | 9.9 ± 3.9* | 39.7 ± 4.8* | 26.7 ± 1.7* | 22.1 ± 4.4 |

Table 6 is an analysis of DNA fragmentation of U-87 MG cells after 72 hour treatment with 25 nM docetaxel. DNA fragmentation may be determined by flow cytometry as described above. Data show percentage of the cell population with DNA fragmentation in all four quadrants of the histogram and represent the Mean±SD of two independent biological replicates (*$p<0.1$).

TABLE 6

|  | 72 hour treatment | | | |
| --- | --- | --- | --- | --- |
|  | DNA Frag (+) Apoptotic bodies (upper left quadrant) | DNA Frag (+) Cells (upper right quadrant) | DNA Frag (−) Cells (lower right quadrant) | DNA Frag (−) Apoptotic bodies (lower left quadrant) |
| DMSO | 0.06 ± 0.06 | 1.70 ± 1.70 | 97.6 ± 2.12 | 0.72 ± 0.39 |
| Docetaxel | 0.10 ± 0.0 | 2.11 ± 1.69 | 94.2 ± 0.07 | 3.57 ± 1.65 |

Test data presented herein demonstrates that resonance generating electromagnetic fields may reduce cell growth, alter cell cycle kinetics, and increase DNA fragmentation in U-87 MG cells. While resonance generating electromagnetic fields at slow modulation may show an increase (e.g., significant increase) in DNA fragmentation; neither Annexin V staining nor caspase-3/7 activation in U-87 MG cells seems correlated to the induction of apoptosis. Exposure of U-87 MG cells to resonance generating electromagnetic fields at fast modulation may decrease total cell number by 30%, similar to slow modulation; however, at fast modulation, there may be an increase (e.g., significant increase) in the sub G0 population (indicative of the formation of apoptotic bodies) and DNA fragmentation. Data suggests that resonant electromagnetic fields, at both slow and fast modulation, induce DNA fragmentation and cell death by a novel mechanism that does not require caspase-3/7 activation, or exposure of PS on the outer leaflet of the dying cell. Treatment of U87-MG cells with 25 nM Docetaxel for 72 hours may induce a 20% decrease in cell number and an increase (e.g., significant increase) in the sub G0 population, and caspase 3/7 activation. Along with increases in PS exposure as measured by Annexin V, classical apoptotic pathways are present in these cells and can be activated with the appropriate stimulus. Both resonance generating electromagnetic fields and docetaxel appear to induce G2/M arrest followed by cell death. Because the induction of mitotic cell death after treatment with docetaxel induces caspase-3/7, while resonance generating electromagnetic fields do not, intracellular mechanisms mediating resonance generating electromagnetic fields induced DNA fragmentation may be different from pathways utilized by both docetaxel and temozolomide that show equivalent results in cell culture. Comparison of the effects of resonance generating electromagnetic fields and docetaxel on U-87 MG cell number shows that resonance generating electromagnetic fields at both slow and fast modulation may be as good as, or better than, docetaxel monotherapy in culture.

Unlike conventional electromagnetic treatments, the use of reference materials may capture one or more exact resonant frequencies and harmonics of a target without having to calculate the appropriate resonant frequency or determine an effective resonant frequency for a particular outcome by trial-and-error. In addition, unlike TTFields, there are unlikely to be unwanted dermatologic side effects. Some embodiments herein may use four different macromolecular targets as reference materials, which may be equally effective, or some may be more effective than others. The effects of targets may be additive or synergistic.

Targets may be optimized based on genome wide comparisons of the common genetic lesions among glioblastoma tumors. Optimization may identify one or more combinations of reference materials for treatment of specific subsets of tumors. For example, tumors with IDH mutations may be targeted more effectively with reference materials based on known IDH mutations, while tumors known to harbor other mutations may not be affected. The effects of resonance generating electromagnetic fields described herein, with the possible exception of cell cycle kinetics after exposure to slow modulation, may be reversed in surviving cells when they are no longer exposed to a field. Thus, the present disclosure may determine whether patients with GBM will require longer term, intermittent, or continual exposure to resonance generating electromagnetic fields to stop growth and progression of GBM. The re-initiation of cell growth noted when the cells are removed from the field may relate to the enrichment of glioblastoma stem-like cells among the surviving population. These stem-like cells may be effectively targeted concurrently using reference antennae with OLIG2 and SALL2 as targets to self-tune the resonance generating electromagnetic fields to reduce or prevent the initiation of cell growth.

Given the advantage of inexpensive whole genome sequencing analysis, one may obtain individualized deep sequencing data derived from the tumor. This would permit the selection of patient specific targets for the reference antennae, which could be used for second line therapy in combination with other modalities. Xenograft studies may be used to determine whether control of GBM tumor growth can be achieved with intermittent exposure to resonance generating electromagnetic fields. The technology disclosed herein induces a significant inhibitory effect on U-87 MG, and is unlikely to induce toxic or other negative side effects. Thus, the possibility of repetitive therapy sessions using resonance generating electromagnetic fields may create valuable medical options and a paradigm shift in cancer therapy.

Further Details on the Effect of Resonance Generating Electromagnetic Fields

Resonance generating electromagnetic fields disclosed herein bring about unique effects. Some electromagnetic fields may give rise to ion cyclotron resonance in two ways when charged particles are moving within a uniform magnetic field: (i) setting an AC peak intensity equal to a static magnetic field; and (ii) when a linearly polarized oscillating electric field is aligned 90° to a static magnetic field. In either case, resonance for a particular ion (e.g., Ca2+, K+) can occur at the same modulation frequency given an equivalent angular velocity and an appropriate, but different field strength. In an RF/low microwave frequency range, the spatial period of an electromagnetic wave emitted by a conventional antenna is much longer than typical molecular sizes. This means that the amplitude may be the same for any part of the molecule, that is, a molecule interacts with spatially homogeneous electric and magnetic fields but varying in time. Electrodynamics says that such an electric field results in rotation of molecules that have a finite dipole moment.

The present disclosure uses, according to some embodiments, multi-solenoidal antennae that are distinct from conventional dipole antennae to produce resonance generating electromagnetic fields. A generated field is proportional to the second derivative of an electric current. Multi-solenoidal antennae may produce even static-like electric and/or magnetic fields, which are proportional to the third and higher-order time derivatives of a current.

Modulation of electromagnetic fields may excite cyclotron and other resonances. Prolonged exposure to amplified resonances may produce a measurable effect, such as a change in spectra and/or biological activity.

Figure 13:
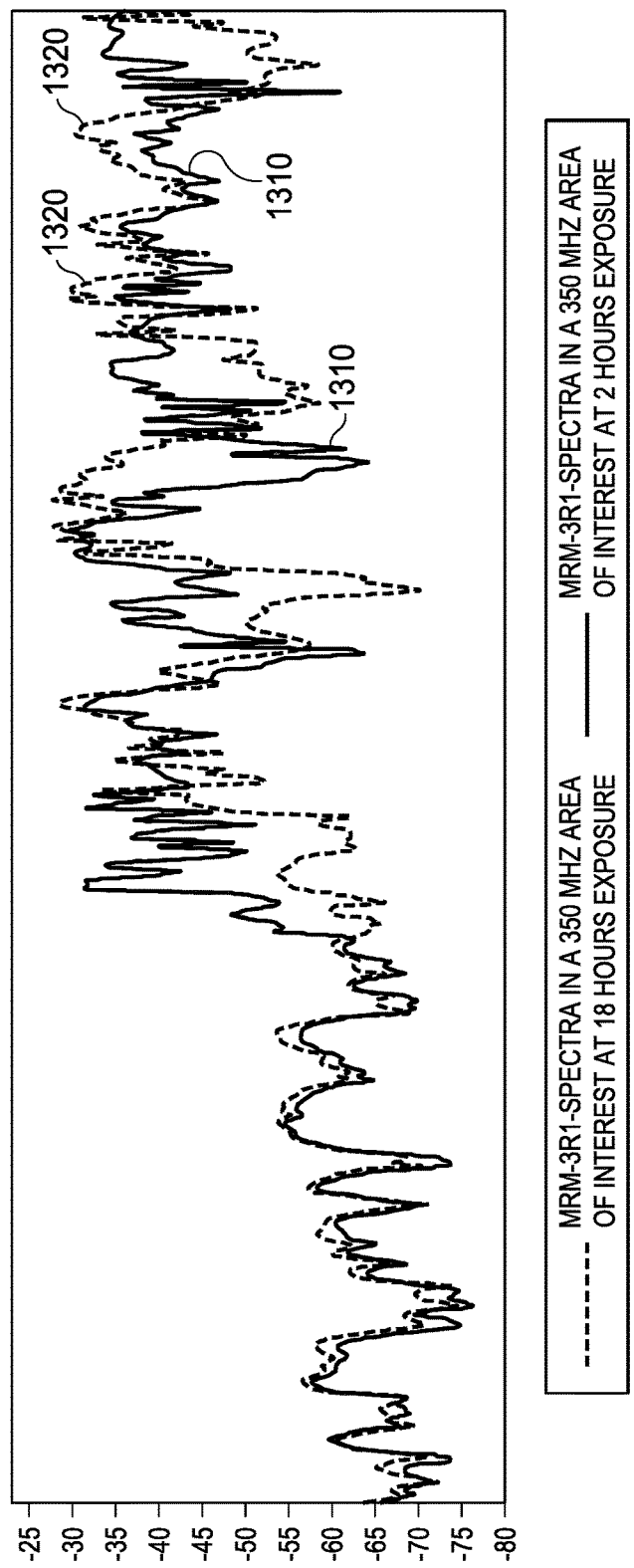
FIG. 13 illustrates a change in spectra from cultures exposed for two hours (represented by curve 1310) and the same cultures after being exposed for 18 hours (represented by curve 1320).

FIG. 13 illustrates a change in spectra from cultures exposed for two hours (represented by curve 1310) and the same cultures after being exposed for 18 hours (represented by curve 1320). Specifically, FIG. 13 shows spectra in a 350 MHz area of interest resulting from U-87 MG cells exposed to resonance generating electromagnetic fields tuned for four, U-87 MG macromolecules taken inside an RF/EMI shield room.

Resonance generating electromagnetic fields disclosed herein may have several useful elements, e.g., (i) antennae that transmit/receive RF/low band microwave radiation in an ultra-wide spectral range; (ii) the properties of disclosed RF/low microwave are distinct from what is radiated by conventional antennae and also those of noise, and these properties make it possible to excite electromagnetic resonances that cannot be excited by conventional RF waves/microwaves; and, (iii) an optional continuous, self-tuning, positive feedback circuit that includes reference material targets specific to the biological substance being treated. These characteristics may enable accurate tuning of resonance generating electromagnetic fields that are otherwise unavailable for various reasons. For example, ion cyclotron resonance is related to field strength and angular velocity of the waveform. As a case in point, separate experiments on bone growth demonstrate that, for the same modulation frequency (16 Hz) and different field intensities (20.9 µT and 40.7 µT), first inducing ion cyclotron resonance of Ca2+ increases bone growth and second inducing ion cyclotron resonance of K+ inhibits bone growth. For another example, ion cyclotron resonance may also occur at higher harmonics of a fundamental resonance frequency. Because resonance generating electromagnetic fields may be generated within a broadband frequency range, harmonic resonance may enhance the effect of these fields on target(s). For yet another example, unlike conventional monochromatic electromagnetic fields without a feedback loop that may be affected by field strength variations, damping and other factors herein give resonance generating electromagnetic fields advantages in application.

As will be understood by those skilled in the art who have the benefit of the instant disclosure, other equivalent or alternative compositions, devices, methods, and systems for resonance-based disease treatment can be envisioned without departing from the description contained herein. Accordingly, the manner of carrying out the disclosure as shown and described is to be construed as illustrative only.

Persons skilled in the art may make various changes in the nature, number, and/or arrangement of parts or steps without departing from the scope of the instant disclosure. For example, the size of a device and/or system may be scaled up or down to suit the needs and/or desires of a practitioner. Each disclosed method and method step may be performed in association with any other disclosed method or method step and in any order according to some embodiments. Where the verb "may" or "can" appears, it is intended to convey an optional and/or permissive condition, but its use is not intended to suggest any lack of operability unless otherwise indicated. Where open terms such as "having" or "comprising" are used, one of ordinary skill in the art having the benefit of the instant disclosure will appreciate that the disclosed features or steps optionally may be combined with additional features or steps. Where "based on" or "based upon" is used, one of ordinary skill in the art having the benefit of the instant disclosure will appreciate that it means one thing is dependent at least in part on another thing, directly or indirectly, exclusively or non-exclusively. Such option may not be exercised and, indeed, in some embodiments, disclosed systems, compositions, apparatuses, and/or methods may exclude any other features or steps beyond those disclosed herein. Elements, compositions, devices, systems, methods, and method steps not recited may be included or excluded as desired or required. Persons skilled in the art may make various changes in methods of preparing and using a composition, device, and/or system of the disclosure.

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value +/−about 10%, depicted value +/−about 50%, depicted value +/−about 100%) and/or a range endpoint. With respect to the former, a value of 50 depicted in an example, table, and/or drawing may form the basis of a range of, for example, about 45 to about 55, about 25 to about 100, and/or about 0 to about 100.

All or a portion of a device and/or system for disease treatment may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

Headings (e.g., Title, Abstract, Background, Detailed Description) are provided in compliance with regulations and/or for the convenience of the reader. They do not include and should not be read to include definitive or over-arching admissions as to the scope and content of prior art or limitations applicable to all disclosed embodiments.

What is claimed is:

1. A method for administering to a subject having or at risk of having a disease condition resonance-based electromagnetic radiation, the method comprising:
    selecting one or more reference materials related to the disease condition;
    capturing one or more resonant frequencies of the reference materials;
    generating a resonant frequency signal comprising at least one of the captured resonant frequencies;
    generating a modulated broadband signal that is simultaneously modulated, in a signal generator, by a first waveform at a first frequency and at least a second waveform at a second frequency;
    radiating an electromagnetic field based on the resonant frequency signal; and
    exposing the subject to the electromagnetic field to affect biological activities of cells related to the disease condition,
    wherein the electromagnetic field is effectuated based on both the resonant frequency signal and the modulated broadband signal.

2. The method of claim 1, further comprising generating, by the signal generator, a booster signal comprising a single, low frequency waveform having a frequency lower than 100 KHz, wherein the electromagnetic field is effectuated further based on the booster signal, and wherein the first frequency of the first waveform is substantially identical with the low frequency of the booster signal but different from the second frequency of the second waveform.

3. The method of claim 2, wherein the modulated broadband signal is received by a first broadband antenna via cable, wherein the booster signal and the resonant frequency signal are received by a second broadband antenna via cables, and wherein the electromagnetic field used to expose the subject is effectuated based on radiations from both the first and second broadband antennae, which are coupled in an antenna box.

4. The method of claim 2, wherein, the modulated broadband signal has a bandwidth of 1 MHz or greater, and wherein the first frequency of the first waveform is about 1 Hz or about 4 Hz, whereas the second frequency of the second waveform is less than 1 MHz.

5. A method for administering to a subject having or at risk of having a disease condition resonance-based electromagnetic radiation, the method comprising:
    selecting one or more first reference materials related to the disease condition;
    capturing one or more first resonant frequencies of the reference materials;
    generating a first resonant frequency signal comprising at least one of the captured resonant frequencies;
    radiating a first electromagnetic field based on the first resonant frequency signal; and
    exposing the subject to the first electromagnetic field to affect biological activities of cells related to the disease condition,
    wherein the one or more reference materials are critical to the function, progression, viability, and/or continuation of a cell or organism causing or associated with the disease condition, and wherein the resonant frequency signal comprises at least two captured resonant frequencies, including any harmonics that are used simultaneously to expose the subject.

6. The method of claim 5, further comprising:
    selecting one or more second reference materials related to the disease condition;
    capturing one or more second resonant frequencies of the second reference materials;
    generating a second resonant frequency signal comprising at least one of the captured second resonant frequencies;
    radiating a second electromagnetic field based on the second resonant frequency signal; and
    exposing the subject to the second electromagnetic field simultaneously with exposure to the electromagnetic field.

7. The method of claim 1, further comprising tuning frequencies of the electromagnetic field via a feedback loop to maximize resonance of the reference materials.

8. The method of claim 1, further comprising, after selecting the reference materials but before capturing the one or more resonant frequencies, placing and isolating the reference materials inside a shielded container, wherein the exposure of the subject to the electromagnetic field lasts for a sufficient cumulative period of time to cause death of cells related to the disease condition or slow the progression of the disease condition.

9. The method of claim 5, wherein the disease condition relates to Glioblastoma Multiforme (GBM), and wherein the one or more reference materials are selected from the group consisting of hsa-miRNA-38, mutated alpha-kinase 2 gene, Hsp70 (70 kDa heat shock protein), CHI3L1 (chitinase-3-like protein 1), and GBM cells.

10. An electromagnetic resonance-based disease treatment system comprising:
    a processing unit configured to generate a resonant frequency signal that carries at least one frequency at which reference materials related to a disease condition resonate; and
    a radiating antenna configured to radiate an electromagnetic field based on the resonant frequency signal,
    wherein the electromagnetic field is operable on a subject having or at risk of having the disease condition by exposing the subject to the electromagnetic field in order to treat the disease condition, wherein the processing unit comprises a signal generator configured to generate a modulated broadband signal at least via simultaneously modulation by a first waveform at a first frequency and at least a second waveform at a second frequency, wherein the electromagnetic field is effectuated based on both the resonant frequency signal and the modulated broadband signal, wherein the signal generator is further configured to generate a booster signal comprising a single, low frequency waveform below about 100 KHz, wherein the electromagnetic field is further based on the booster signal, and wherein the first frequency of the first waveform is substantially identical with the low frequency of the booster signal but different from the second frequency of the second waveform.

11. The system of claim 10, wherein the resonant frequency signal carries a plurality of resonant frequencies that are used simultaneously to expose the subject.

12. The system of claim 11, wherein the processing unit comprises a multi-frequency signal generator or multiple single frequency signal generators configured to generate the plurality of resonant frequencies based on calculated, digitized, or measured resonant frequencies of the reference materials.

13. The system of claim 10, further comprising:
a feedback antenna located in a near field zone of the subject; and
an amplifier coupled to the feedback antenna and the radiating antenna,
wherein the feedback antenna, the amplifier, and the radiating antenna form a feedback loop operable to tune frequencies of the electromagnetic field.

14. A system for administering to a subject a resonance-based electromagnetic radiation, the system comprising:
means for selecting one or more target substances relevant to a disease condition; and
means for determining at least one resonant frequency at which the target substances resonate;
means for generating a broadband signal that is simultaneously modulated at two frequencies of two different waveforms;
means for generating a resonant frequency signal comprising the at least one resonant frequency;
means for radiating an electromagnetic field based on the broadband signal and the resonant frequency signal; and
means for exposing a subject carrying the disease condition to the electromagnetic field to affect biological activities of cells relevant to the disease condition.

* * * * *